US007968082B1

(12) United States Patent (10) Patent No.: US 7,968,082 B1
Shriver et al. (45) Date of Patent: Jun. 28, 2011

(54) EVALUATING MIXTURES OF LOW MOLECULAR WEIGHT HEPARINS BY NMR

(75) Inventors: Zachary Shriver, Cambridge, MA (US); Daniela Beccati, Brighton, MA (US); Ishan Capila, Ashland, MA (US); Jonathan Lansing, Reading, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 619 days.

(21) Appl. No.: 12/011,308

(22) Filed: Jan. 25, 2008

Related U.S. Application Data

(60) Provisional application No. 60/886,724, filed on Jan. 26, 2007.

(51) Int. Cl.
*A61B 5/055* (2006.01)
*A61K 31/727* (2006.01)
(52) U.S. Cl. .................... 424/9.3; 514/56; 505/844
(58) Field of Classification Search ............... 424/9.3; 514/56; 505/844
See application file for complete search history.

(56) References Cited

U.S. PATENT DOCUMENTS

| | | | |
|---|---|---|---|
| 4,692,435 | A | 9/1987 | Lormeau |
| 5,389,618 | A | 2/1995 | Debrie |
| 6,617,316 | B1 | 9/2003 | Mourier et al. |
| RE38,743 | E | 6/2005 | Debrie |
| 7,083,937 | B2 | 8/2006 | Sasisekharan et al. |
| 7,585,642 | B2 | 9/2009 | Sasisekharan et al. |
| 2002/0169143 | A1 | 11/2002 | Sasisekharan et al. |
| 2003/0203385 | A1 | 10/2003 | Venkataraman et al. |
| 2004/0265943 | A1 | 12/2004 | Viskov et al. |
| 2005/0119477 | A1 | 6/2005 | Mourier et al. |
| 2005/0186679 | A1 | 8/2005 | Viskov et al. |
| 2005/0215519 | A1 | 9/2005 | Viskov et al. |
| 2005/0288252 | A1 | 12/2005 | Nurcombe et al. |
| 2006/0024664 | A1 | 2/2006 | Sasisekharan et al. |
| 2007/0065921 | A1 | 3/2007 | Sasisekharan et al. |
| 2007/0098708 | A1 | 5/2007 | Myette |
| 2007/0161073 | A1 | 7/2007 | Sasisekharan et al. |
| 2007/0287683 | A1 | 12/2007 | Shriver et al. |
| 2008/0009069 | A1 | 1/2008 | Mourier et al. |

FOREIGN PATENT DOCUMENTS

| | | |
|---|---|---|
| EP | 1580197 | 9/2005 |
| EP | 1582531 | 10/2005 |
| EP | 1586588 | 10/2005 |
| WO | WO9003791 A1 | 4/1990 |
| WO | WO 01/29055 | 4/2001 |
| WO | WO 03/078960 | 9/2003 |
| WO | WO 2004/027087 | 4/2004 |
| WO | WO 2005/009040 | 1/2005 |
| WO | WO 2005/080438 | 9/2005 |
| WO | WO 2005/090411 | 9/2005 |

OTHER PUBLICATIONS

Campbell, S.A. (2004) Filed by Amphastar Pharmaceuticals in Response to Citizen Petition Docket No. 03P-0064/CP1 filed with the United States Food and Drug Administration. Response filed on May 13, 2004, Entered inito FDA docket system on Jun. 8, 2004.*
Ansel, H.C., Allen, Jr., L.V., Popovich, N.G. (1999) Pharmaceutical Dosage Forms and Drug Delivery Systems. Published by Lippincott Williams & Wilkins, p. 23-27 and 54-59.*
Yates, E.A., Santini, F., Guerrini, M., Naggi, A., Torri, G., Casu, B. (1996) 1H and 13C NMR spectral assignments of the major sequences of twelve systematically modified heparin derivatives. Carbohydrate Research, vol. 294, p. 15-27.*
Guerrini, M., Naggi, Guglieri, S., Santarsiero, R., Torri,G. (2005) Complex glycosaminoglycans: profiling substitution patterns by two-dimensional nuclear magnetic resonance spectroscopy. Analytical Biochemistry, vol. 337, p. 35-47.*
Piani, S., Casu, B., Marchi, E.G., Torri, G., Ungarelli, F. (1993) Alkali-Induced Optical Rotation Changes in Heparins and Heparan Sulfates, and Their Relation to Iduronic Acid-Containing Sequences. Journal of Carbohydrate Chemistry, vol. 12, No. 4&5, p. 507-521.*
Hricovini, M., Guerrini, M., Torri, G., Piani, S., Ungarelli. F. (1995) Conformational analysis of heparin epoxide in aqueous solution. An NMR relaxation study. Carbohydrate Research, vol. 277, p. 11-23.*
Perlin, A.S., Casu, B. (1982) Spectroscopic Methods in The Polysaccharides. Edited by G.O. Aspinall, published by Academic Press, vol. 1, p. 133-193.*
Guerrini, M., Bisio, A., Torri, G. (2001) Combined Quantitative 1H and 13C Nuclear Magnetic Resonance Spectroscopy for Characterization of Heparin Preparations. Seminars in Thrombosis and Hemostasis, vol. 27, No. 5, p. 473-482.*
Ampofo, S. et al., "Disaccharide Compositional Analysis of Heparin and Heparan Sulfate Using Capillary Zone Electrophoresis," *Analytical Biochem.*, 199:249-255 (1991).
Da Col, R. et al., "Characterization of the Chemical Structure of Sulphated Glycosaminoglycans After Enzymatic Digestion. Application for Liquid Chromatography-Mass Spectrometry with an Atmospheric Pressure Interface," *J. of Chromatography*, 647:289-300 (1993).
Desai, U. et al., "Oligosaccharide Composition of Heparin and Low-molecular-weight Heparins by Capillary Electrophoresis," *Analytical Biochem.*, 213:120-127 (1993).
Ernst, S. et al., "Direct Evidence for Predominantly Exolytic Processive Mechanism for Depolymerization of Heparin-like Glycosaminoglycans by Heparinase I," *PNAS*, 95:4182-4187 (1998).
Guo, Y. et al., "The Disaccharide of Heparins and Heparan Sulfates," *Analytical Biochem.*, 176:96-104 (1989).
Imanari, T. et al., "High-performance Liquid Chromatographic Analysis of Glycosaminoglycan-derived Oligosaccharides," *J. of Chromatography A*, 720:275-293 (1996).
Karamanos, N. et al., "Ion-pair High-performance Liquid Chromatography for Determining Disaccharide Composition in Heparin and Heparan Sulphate," *J. of Chromatography A*, 765:169-179 (1997).

(Continued)

*Primary Examiner* — Shaojia Anna Jiang
*Assistant Examiner* — Scarlett Goon
(74) *Attorney, Agent, or Firm* — Lando & Anastasi, LLP

(57) ABSTRACT

Methods for analyzing mixtures of polysaccharides, for example heparin such as enoxaparin are described. In some instances, the mixtures are analyzed using 1D NMR and/or 2D NMR.

21 Claims, 6 Drawing Sheets

OTHER PUBLICATIONS

Kariya, Y. et al., "Disaccharide Analysis of Heparin and Heparan Sulfate Using Deaminative Cleavage with Nitrous Acid and Subsequent Labeling with Paranitrophenyl Hydrazine," *J. Biochem.* (Tokyo), 123(2):240-6 (1998) Abstract Only.

Kinoshita, A. et al., "Microanalysis of Glycosaminoglycan-derived Oligosaccharides Labeled with a Fluorophore 2-aminobenzamide by High-performance Liquid Chromatography: Application to Disaccharide Composition Analysis of Exosequencing of Oligosaccharides," *Analytical Biochem.*, 269:367-378 (1999).

Lamari, F. et al., "Analysis of Glycosaminoglycan-derived Disaccharides in Biologic Samples by Capillary Electrophoresis and Protocol for Sequencing Glycosaminoglycans," *Biomedical Chromatography*, 16:95-102 (2002).

Lee, G. et al., "Separation of Reduced Disaccharides Derived from Glycosaminoglycans by High-performance Liquid Chromatography," *J. of Chromatography*, 212:65-73 (1981).

Lindhart, R. et al., "Mapping and Quantification of the Major Oligosaccharide Components of Heparin," *Biochem. Journal*, 254:781-787 (1988).

Linhardt, R. et al., "Oligosaccharide Mapping of Low Molecular Weight Heparins: Structure and Activity Differences," *J. of Medicinal Chem.*, 33(6):1639-1645 (1990).

Lindhardt, R. et al., "New Methodologies in Heparin Structure Analysis and the Generation of LMW Heparins," *Heparin and Related Polysaccharides*, 37-47, ed. D.A. Lane et al., Plenum Press, New York (1992).

Merchant, K. et al., "Structure of Heparin-derived Tetrasaccharides," Biochem. Journal, 229:369-377 (1985).

Militsopoulou, M. et al., "Determination of 12 Heparin- and Heparan Sulfate-derived Disaccharides as 2-aminoacridone Derivatives by Capillary Zone Electrophoresis Using Ultraviolet and Laser-induced Flourescence Detection," *Electrophoresis*, 23:1104-1109 (2002).

Park, Y. et al., "Purification and Characterization of Heparin Sulphate Proteoglycan from Bovine Brain," Biochem. Journal, 344:723-730 (1999).

Pervin, A. et al., "Separation of Glycosaminoglycan-derived Oligosaccharides by Capillary Electrophoresis Using Reverse Polarity," *Analytical Biochem.*, 221:182-188 (1994).

Rhomberg, A. et al., "Mass Spectrometric and Capillary Electrophoretic Investigation of the Enzymatic Degradation of Heparin-like Glycosaminoglycans," PNAS, 95:4167-4181 (1998).

Rice, K. et al., "High-performance Liquid Chromatographic Separation of Heparin-derived Oligosaccharides," *Analytical Biochem.*, 150(2):325-31 (1985) Abstract Only.

Ruiz-Calero, V. et al., "Pressure-assisted Capillary Electrophoresis-electrospray Ion Trap Mass Spectrometry for the Analysis of Heparin Depolymerised Disaccharides," *J. of Chromatography A*, 914:277-291 (2001).

Ruiz-Calero, V. et al., "Use of Reversed Polarity and a Pressure Gradient in the Analysis of Disaccharide Composition of Heparin by Capillary Electrophoresis," *J. of Chromatography A*, 828:497-508 (1998).

Saad, O. et al., "Compositional Analysis and Quantification of Heparin and Heparan Sulfate by Electrospray Ionization Ion Trap Mass Spectrometry," *Anal. Chem.*, 75:2985-2995 (2003).

Scapol, L. et al., "Capillary Electrophoresis of Heparin and Dermatan Sulfate Unsaturated Disaccharides with Triethylamine and Acetonitrile as Elecrolyte Additives," *J. of Chromatography A.*, 735:367-374, (1996).

Thanawiroon, C. et al., "Separation of a Complex Mixture of Heparin-derived Oligosaccharides Using Reversed-phase High-performance Liquid Chromatography," J. of Chromatography A, 1014:215-223 (2003).

Thanawiroon, C. et al., "Liquid Chromatography/Mass Spectrometry Sequencing Approach for Highly Sulfated Heparin-derived Oligosaccharides," *J. of Biological Chem.*, 279(4):2608-2615 (2004).

Toida, T. et al., "Structural Differences and the Presence of Unsubstituted Amino Groups in Heparan Sulphates from Different Tissues and Species," *Biochem. Journal*, 322:499-506 (1997).

Toyoda, H. et al., "Rapid and Sensitive Analysis of Disaccharide Composition in Heparin and Heparan Sulfate by Reversed-phase Ion-pair Chromatography on a 2 μm Porous Silica Gel Column," *J. of Chromatography A*, 830:197-201 (1999).

Volpi, N., "Characterization of Heparins with Different Relative Molecular Masses (from 11 600 to 1600) by Various Analytical Techniques," *J. of Chromatography*, 622:13-20 (1993).

Volpi, N., "Hyaluronic Acid and Chondroitin Sulfate Unsaturated Disaccharides Analysis by High-Performance Liquid Chromatography and Fluorimetric Detection with Dansylhydrazine," *Analytical Biochem.*, 277:19-24 (2000).

Vynios, D. et al., "Advances in Analysis of Glycosaminoglycans: Its Applications for the Assessment of Physiological and Pathological States of Connective Tissues," *J. of Chromatography B*, 781:21-38 (2002).

Yoshida, K., "Analysis of Unsaturated Disaccharides form Glycosaminoglycuronan by High-performance Liquid Chromatography," *Analytical Biochem.*, 117:327-332 (1989).

Araki et al., "Application of 2-aminopyriopyridine fluorescence labeling in the analysis of in vivo and in vitro metabolism of dextran sulfate sodium by size-exclusion high-proformance liquid chromatography", Journal of Chromatrography B: vol. 753, No. 2 pp. 209-215 (2001).

Alban et al., "Development of SPC-ELISA: A new assay principle for the study of sulfated polysaccharide-protein interactions", Journal of Biomolecular Screening, vol. 6, No. 6, pp. 393-400, (2001).

Jeske et al., Pharmacologic profile of certoparin. Expert Opinion on Investigational drugs, vol. 8, No. 3, pp. 315-327 (1999).

Kuhle et al., "Pharmacokinetic study of Tinzaparin in Pediatric Patients, Blood", vol. 100, No. 11 pp. abstract No. 3975. *abstract only* (2002).

Watt et al., "Comparison of Ovine, bovine and porcine muccosal heparins and low molecular weight heparins by disaccharide analyses and 13 C NMR" Carborhydrate Polymers, vol. 33, pp. 5-11 (1997).

Dawes et al., "The measurement of heparin and other therapeutic sulfated polysaacharides in plasma, serum and urine", Thrombosis and Haemostasis, vol. 54, No. 3, pp. 630-634, (1985).

Van Putten et al., "Determination of low molecular weight heparin in the clinical laboratory" Haemostasis, vol. 14, No. 2 pp. 205-210. (1984).

Guizzardi et al., "Pharmacokinetics and organ distribution in rate of low molecular weight heparin", Arzneimittel-Forschung, vol. 37, No. 11 pp. 1281-1283 (1987).

International Search Report from International Application Serial No.: PCT/US03/07208 dated Nov. 16, 2004.

Supplementary Partial European Search Report from European Application No.; EP037446289 dated Jul. 14, 2008.

Venkataraman, G., "Sequencing complex polysaccharides" vol. 286 (1999).

Desai et al.. "Molecular weight of low molecular weight heparins by 13C nuclear magnetic resonance spectroscopy," Carbohydrate Research, 255, (1994) pp. 193-212.

Malsch et al., "High-resolution capillary electrophoresis and polyacrylamide gel electophoresis of heparins," Journal of Chromatography A. 716. (1995) pp. 258-268.

Sundaram et al., "Rational design of low-molecular weight heparins with improved in vivo activity," PNAS, 100(2), Jan. 21, 2003, pp. 651-656.

Bianchini et al. "Few Bicyclic Acetals at Reducing End of Low-Molecular-Weight Heparins: Might they Restrict Specification of Pharmacopoeia?" Pharmeuropa Scientific Notes, 2005—1 pp. 1-3.

Bianchini et al. "Variability of Heparins and Heterogeneity of Low Molecular Weight Heparins" Seminars in Thrombosis and Hemostasis vol. 33, No. 5 2007 pp. 496-502.

Cerny et al. "Preparation of 2-Amino-1,6-Anhydro-2,3-Dideoxy-B-D-arabino-Hexopyranose. 1H- and 13C-N. M.R. Spectra of Deoxy Derivatives of 2-Amino-1,6-Anhydro-2-Deoxy-D-Glucose and 2-Amino-1,6-Anhydro-2-Deoxy-D-Mannose." Carbohydrate Research, 130 (1984) 103-114.

Fareed et al. "Generic Low-Molecular-Weight Heparins: Some Practical Considerations" Seminars in Thrombosis and Hemostasis. vol. 30, No. 6 2004 pp. 703-713.

Fareed et al. "Biochemical and Pharmacologic Heterogeneity in Low Molecular Weight Heparins. Impact on the Therapeutic Profile" Current Pharmaceutical Design, 2004 vol. 10, 983-999.

Guerrini et al. Low Molecular Weight Heparins: Structural Differentiation by Bidimensional nuclear magnetic Resonance Spectroscopy. Seminars in Thrombosis and Hemostasis. vol. 33, No. 5 2007 pp. 478-487.

Mascellani et al. "Characterization of di- and monosulfated, unsaturated heparin disaccharides with terminal N-sulfated 1,6-anhydro-B-D-glucosamine or N-sulfated 1,6-anhydro-B-D-mannosamine residues" Carbohydrate Research vol. 342 (2007) pp. 835-842.

Citizens Petition filed with the United States Food and Drug Administration by Aventis Pharmaceuticals Inc. on Feb. 19, 2003.

Citizens Petition Supplemental filed with the United States Food and Drug Administration by Aventis Pharmaceuticals Inc. on Feb. 12, 2004.

"2.6.26. Test for Anti-D Antibodies in Intravenous Immunoglobulin" Pharmeuropa vol. 16, No. 1, Jan. 2004 pp. 121-122.

Holzgrabe, U., Deubner, R., Scholl mayer, C., Weibel, B. (2005) Quantitative NMR spectroscopy—Applications in drug analysis. Journal of Pharmaceutical and Biomedical Analysis, v. 38, p. 806-812.

Hirano, S. (1970) NMR study of 4-deoxy-a-L-threo-4-enohexopyranosyluronic acid (1-3)2-acetamido-2-deoxy-D-hexoses produced in the enzymic digestion of hyaluronate, chondroitin and chondroitin sulfates. Organic Magnetic Resonance, vol. 2, p. 577-580.

Mascellani et al. "Characterization of di- and monosulfated, unsaturated heparin disaccharides with terminal N-sulfated 1,6-anhydro-B-D-glucosamine or N-sulfated 1,6-anhydro-B-D-mannosamine residues" Carbohydrate Research vol. 342 (2007) pp. 835-842.

* cited by examiner

EVALUATING MIXTURES OF LOW MOLECULAR WEIGHT HEPARINS BY NMR

This application claims priority to U.S. Provisional Application No. 60/886,724 filed Jan. 26, 2007, the contents of which is incorporated herein in its entirety.

BACKGROUND

The invention relates to methods of analyzing samples containing complex carbohydrates, e.g., low molecular weight heparins (LMWHs), e.g., most preferably enoxaparin, and particularly the use of nuclear magnetic resonance spectroscopy (NMR), e.g., 1D $^1$H NMR, 1D $^{13}$C NMR, 2D homonuclear $^1$H-$^1$H NMR or 2D heteronuclear NMR, such as a 2D $^1$H, $^{13}$C correlation NMR, as applied, e.g., to analyze, control or monitor the production of a LMWH such as enoxaparin. It also relates to useful analytes which can be detected or prepared with the methods described herein.

Complex polysaccharides have been used as pharmaceutical interventions in a number of disease processes, including oncology, inflammatory diseases, and thrombosis. Examples of pharmaceutical interventions in this class are hyaluronic acid, an aid to wound healing and anti-cancer agent, and heparin, a potent anticoagulant and anti-thrombotic agent. Complex polysaccharides function primarily through binding soluble protein signaling molecules, including growth factors, cytokines and morphogens present at the cell surface and within the extracellular matrices between cells, as well as their cognate receptors present within this environment. In so doing, these complex polysaccharides effect critical changes in extracellular and intracellular signaling pathways important to cell and tissue function. For example, heparin binds to the coagulation inhibitor antithrombin III and promoting its ability to inhibit factor IIa and Xa. Being able to identify and quantify the type and extent of chemical modification of a polysaccharide chain as a result of isolation and processing would be of benefit both from (1) a process control standpoint and (2) understanding biologically specific structure-function relationships.

SUMMARY

The analysis of a LMWH, e.g., enoxaparin, e.g., by NMR, e.g., $^1$H NMR or 2D NMR, can be used to evaluate starting materials, processes, intermediates and final products in the production of LMWHs, particularly enoxaparin. The presence, distribution, or amount of a structure or species described herein can be used in these evaluations.

By way of example, NMR, e.g., $^1$H NMR analysis of a preparation of enoxaparin can provide information about the presence, distribution, or amount of a subject entity, e.g., a peak, signal, structure or species described in Table 2. Accordingly, a preparation of enoxaparin can be evaluated by determining the presence, distribution, or amount of one or more of the structures in Table 2. Although the structures in Table 2 are derived from enoxaparin, all may also occur in other LMWHs and can therefore be used in the evaluation of other LMWHs.

By way of further example, 2D NMR, can be used to provide information about the presence, distribution, or amount of a subject entity, e.g., a structure or species described in Table 3. Although the structures in Table 3 are derived from enoxaparin, all may also occur in other LMWHs and can therefore be used in the evaluation of other LMWHs.

Methods disclosed herein are useful in analyzing or processing a LMWH preparation, e.g., to determine whether to accept or reject a batch of a LMWH, e.g., enoxaparin, or to guide the control of a step in the production of a LMWH, e.g., enoxaparin.

The methods described herein can be used with LMWHs, and in particular enoxaparin. Enoxaparin is the preferred LMWH and the examples and much of the discussion is directed to enoxaparin. The methods described herein can, though, be applied to other LMWHs. In some cases the methods are directly applicable and in some one of ordinary skill in the art will appreciate that modifications may be needed and can institute those as guided by the art and this disclosure.

In one aspect, the invention provides, a method of evaluating or processing a polysaccharide mixture, e.g., a LMWH preparation, e.g., an enoxaparin preparation.

The method includes:

providing an evaluation of a parameter related to a subject entity, e.g., a peak, signal, structure or species described herein, e.g., a subject entity listed in Table 1, Table 2, Table 3 or Table 4. Such parameters can include, or be a function of, the presence, relative distribution, or amount of a subject entity, e.g., a structure disclosed herein, and, optionally, providing a determination of whether a value (e.g., a value correlated to the presence, absence, or amount) determined for the parameter meets a preselected criterion, e.g., is present or is present within a preselected range, thereby evaluating or processing the mixture.

In a preferred embodiment, the method includes providing a comparison of the value or position determined for a parameter with a reference value or values, to thereby evaluate the sample. In preferred embodiments, the comparison includes determining if the test value has a preselected relationship with the reference value, e.g., determining if it meets the reference value. The value need not be a numerical value but can be merely an indication of whether the subject entity is present.

In a preferred embodiment the method includes determining if a test value is equal to or greater than a reference value, if it is less than or equal to a reference value, or if it falls within a range (either inclusive or exclusive of one or both endpoints). By way of example, the amount of a structure listed in Table 2 or Table 3 can be determined and, optionally shown to fall within a preselected range, e.g., a range which corresponds to a range from Table 2 or a range which corresponds to a range from Table 3.

In preferred embodiments, the test value, or an indication of whether the preselected criterion is met, can be memorialized, e.g., in a computer readable record.

In preferred embodiments, a decision or step is taken, e.g., the sample is classified, selected, accepted or discarded, released or withheld, processed into a drug product, shipped, moved to a different location, formulated, labeled, packaged, released into commerce, or sold or offered for sale, depending on whether the preselected criterion is met. E.g., based on the result of the determination or whether one or more subject entities is present, or upon comparison to a reference standard, the batch from which the sample is taken can be processed, e.g., as just described.

As mentioned above, the methods disclosed herein can include evaluating the presence, distribution, or amount of a selected subject entity, e.g., a structure or species, e.g., a selected chemical structure or species present in a sample or a selected chemical structure or species absent from a sample. Examples of a species include contaminant species present in a sample, e.g., non-UFH glycosaminoglycan contaminants, such as dermatan sulfate. A structure can be, e.g., a structure present in one or more saccharide structures. Examples of structures include selected, inter-saccharide linkages, terminal groups, epimeric forms, the presence or location of a derivative moiety, e.g., a sulfate or an acetyl group, an anhydro form, or 2, 3 epoxide.

A particularly preferred structure, e.g., with regard to structures in Table 1, is an acetyl moiety, a sulfate moiety, a glucosamine residue, or a uronate residue. Examples of preferred structures include the methyl signal of the N-acetyl group (3 protons), H-2 of N-sulfated glucosamine residues, H-2 of glucuronic acid and H-2 of 3-O-sulfated glucosamine, H-1 of IdoAp2-OH, H-1 of IdoAp2S, H-1 of 3-O-sulfated glucosamine residues and H-1 of ΔUAp2S residue, H-4 of ΔUAp2-OH residue, and H-4 of ΔUAp2S residue.

A particularly preferred structure, e.g., with regard to structures in Table 2, is a glucosamine residue (e.g., N-sulfated, 3-O, N-sulfated, or N-acetyl) or a uronate residue (e.g., 2-O sulfated, unsulfated, or iduronic acid (Ido A)/glucuronic acid (GlcA)).

A particularly preferred structure, e.g., with regard to structures in Table 3, is a hexosamine residue, for example, total N-sulfated hexosamine ($H_{NS}$) such as $H_{NS}$-G, $H_{NS}$-I, 1,6 anhydro mannosamine (An Man), and 1,6 anhydro glucosamine (An Glc), a total of 1,6 anhydro moieties, 3-O-sulfated glucosamine ($H_{NS,3S,6S}$), N-acetyl glucosamine ($H_{NAc}$), or 6-O-sulfated glucosamine ($H_{6S}$); or a uronic acid residue, for example, a 2-O-sulfated uronic acid such as $I_{2S,red}$, or $G_{2S}$, or a non-sulfated uronic acid such as I-$H_{NS/Ac,6S}$, I-$H_{NS/Ac}$, G-$H_{NS}$, or G-$H_{NAc}$.

In some embodiments, NMR analysis of a complex mixture, e.g., a polysaccharide mixture such as an enoxaparin preparation, can be completed without any modification of the mixture such as chemical or enzymatic digestion of a polysaccharide mixture (for example the sort of digestion used for other analytical techniques such as RPHPLC).

In some embodiments, analysis of a polysaccharide mixture without prior chemical or enzymatic digestion can provide information not available using a technique requiring such digestion. For example, enzymatic digestion of polysaccharide mixtures such as an enoxaparin preparation can chemically alter one or more saccharide moieties such that information about the starting material would no longer be available for chemical analysis. In the case of enzymatic digestion of a polysaccharide mixture containing uronic acid, the epimerization state of the uronic acid cannot be determined after enzymatic digestion due to conversion of both isomers to a unsaturated uronic acid having a 4,5 double bond (ΔU). Accordingly, a method described herein using either 1D NMR or 2D NMR, can provide information, for example about the epimerization state of an uronic acid moiety in a polysaccharide mixture that would not be available using some other analytical techniques.

The evaluation of the presence or distribution of a subject entity, e.g., a structure or specie or species can show if the subject entity or a LMWH preparation, e.g., an enoxaparin preparation, meets a reference standard.

In preferred embodiments, methods and compositions disclosed herein are useful from a process standpoint, e.g., to monitor or ensure batch-to-batch consistency or quality, or to evaluate a sample with regard to a reference, e.g., a preselected value.

In preferred embodiments, methods and compositions disclosed herein can be used to determine if a test batch of a LMWH, e.g., an enoxaparin, can be expected to have one or more of the properties of a LMWH, e.g., an enoxaparin. Such properties can include a property listed on the product insert of a LMWH, e.g., an enoxaparin, a property appearing in a compendium, e.g., the US Pharmacopea, or a property required by a regulatory agency, e.g., the FDA, for commercial use. A determination made by a method disclosed herein can be a direct or indirect measure of such a property. E.g., a direct measurement can be where the desired property is a preselected level of the subject entity being measured. In an indirect measurement the measured subject entity is correlated with, or is a proxy for a desired property, e.g., a property described herein. Exemplary properties for enoxaparin include:

A preselected level of anti-XA activity, e.g., between 75 IU/mg-150 IU/mg and preferably about 100 IU/mg;

A preselected level of anti-IIA activity, e.g., between 20-35 and preferably about 30 IU/mg;

A preselected ratio of anti-XA/anti-IIA activity, e.g., between 3.3-5.3 and preferably about 4;

A preselected value for average molecular weight, e.g., between 4300-4800 Da and preferably about 4500 Da;

A set of preselected value for molecular weight distribution, e.g., about 12-20% and preferably 16% are <2000 Da species, greater than or equal to 68-82% and preferably greater than or equal to 68% are 2000-8000 Da species; and less than or equal to 18% are >8000 Da species;

A preselected level of chains ending in a 1,6-anhydro linkage, e.g., between 15-30% and preferably about 15-25% or 20-30%, e.g., as measured by weight average molecular weight or total % of chain;

A preselected level of chains ending in a 1,6-anhydro linkage, e.g., between 15-30% and preferably about 15-25% or 20-30%, e.g., as measured by weight average, molecular weight or total percent of chains; or A preselected value for glycoserine, 1-5 mole % e.g., less than 0.3% and preferably less than 0.2%, or less than 0.1%.

Methods and compositions disclosed herein can be used where the presence or distribution, of one or more structure or species in the mixture may possess or impinge on the biological activity.

The methods are also useful from a structure-activity prospective, to evaluate or ensure biological equivalence.

In a preferred embodiment, the sample is analyzed by 1D NMR. In one embodiment, method includes: providing a heparin preparation, e.g., an enoxaparin preparation; obtaining a proton NMR, e.g., a $^1$H 1D NMR of the preparation; and, optionally, evaluating the presence distribution or amount of a selected subject entity, e.g., a structure or species described herein. In one embodiment, the method can include identifying and/or quantifying at least a first proton associated with a structure of the preparation, thereby allowing analysis, e.g., qualitative and/or quantitative analysis, of said structure in the preparation.

In one embodiment, the enoxaparin sample is size fractionated. In one embodiment, the enoxaparin sample includes or consists of one or more fractions of tetrasaccharides, hexasaccharides, octasaccharides, decasaccharides, dodecasaccharides and tetradecasaccharides, or a sample enriched for one or more of these classes.

In one embodiment, the 1D NMR is a 1D NMR method described herein, e.g., a $^1$H NMR method. In one embodiment, the 1D NMR method includes a recycle delay, e.g., a recycle delay greater than the longitudinal relaxation time (T1) of the slowest relaxing proton in the preparation. For example, the recycle delay can be 2, 3, 4, 5, 6, 7, 8, 9, 10 times the T1 of the slowest relaxing proton in the preparation, preferably about 5 times the T1 of the slowest relaxing proton in the preparation.

In a preferred embodiment a saccharide structure is evaluated using, $^1$H NMR, where one or more acidic hydrogens have been exchanged with deuterium, e.g., a sample of a polysaccharide mixture is exchanged with $D_2O$, lyophilized over night, and redissolved in $D_2O$.

In one embodiment, the structure can be naturally associated with a starting material, e.g., unfractionated heparin. In another embodiment, the structure can be a structure that is not naturally associated with a starting material, e.g., a structure not naturally present in a chain of unfractionated heparin. For example, a structure not naturally associated with the starting material (also referred to herein as a "modified structure") can be, e.g., a structure resulting from a method used to make a LMWH sample. In one embodiment, the preparation is an enoxaparin preparation and the modified structure can be one or more of: a mannosamine, a uronate at the reducing end, and a galacturonic acid. In one embodiment, the method includes determining if one or more reducing end and/or non-reducing end structural moiety is present in the sample. In one embodiment, one or more of the protons identified is associated with an epimerized state of a uronic acid, e.g., iduronic acid and/or glucuronic acid, e.g., a 2-O sulfated and/or unsulfated iduronic acid, glucuronic acid or combinations thereof. In one embodiment, one or more of the protons identified is associated with a uronic acid having a Δ4,5 double bond, e.g., a sulfated and/or non-sulfated uronic acid having a Δ4,5 double bond. In one embodiment, one or more protons identified is associated with a glucosamine, e.g., a glucosamine having one or more of the following properties: N-acetylated, N-sulfated, and 3-O sulfated. In one embodiment, one or more protons identified is associated with a mannosamine. In another embodiment, the method identifies a glycosidic linkage associated with a structural moiety.

For example, a method described herein can be used to detect the presence of a subject entity provided in Table 1 such as a methyl signal of an N-acetyl group (3 protons), an H-2 of N-sulfated an glucosamine residue, an H-2 of a glucuronic acid, an H-2 of a 3-O-sulfated glucosamine, an H-1 of an IdoAp2-OH, an H-1 of an IdoAp2S, an H-1 of a 3-O-sulfated glucosamine residue, an H-1 of a ΔUAp2S residue, an H-4 of a ΔUAp2-OH residue, and an H-4 of a ΔUAp2S residue. One or more of the peaks representing on or more structures of Table 1 can be integrated to provide relative monosaccharide percentage composition for the categories of monosaccharides included with the eight peaks described in Table 1. By way of example, peak P1 has three protons, therefore its area is divided by three. Peaks P3 and P6 consist of overlapping signals from two different monosaccharide signatures, so the individual contributions are generally calculated from these peaks by subtraction. All other areas referred to in Table 1 represent one proton only.

TABLE 1

| Peak Number | Chemical Shift (ppm)* | Assignment |
|---|---|---|
| P1 | 1.95-2.05 | Methyl signal of the N-acetyl group (3 protons) |
| P2 | 3.15-3.29 | H-2 of N-sulfated glucosamine residues |
| P3 | 3.32-3.49 | H-2 of glucuronic acid + H-2 of 3-O-sulfated glucosamine |
| P4 | 4.96-5.00 | H-1 of IdoAp2-OH |
| P5 | 5.10-5.24 | H-1 of IdoAp2S |
| P6 | 5.46-5.52 | H-1 of 3-O-sulfated glucosamine residues + H-1 of ΔUAp2S residue |
| P7 | 5.75-5.87 | H-4 of ΔUAp2-OH residue |
| P8 | 5.90-6.05 | H-4 of ΔUAp2S residue |

In one embodiment, one or more structures have a proton detected at about: 1.85 to 2.15 ppm (e.g., 2.05 ppm, e.g., 2.00 ppm, e.g., 1.95 ppm); 3.05 to 3.40 ppm (e.g., 3.15 to 3.30 ppm, e.g., 3.20 to 3.25 ppm); 3.30 to 3.60 (e.g., 3,32, to 3.49); 4.85 to 5.10 ppm (e.g., 4.95 to 5.00 ppm); 5.05 to 5.30 ppm (e.g., 5.10 to 5.25 ppm); e.g., 5.40 to 5.60 (e.g., e.g., 5.45 to 5.55 ppm); 5.70 to 5.90 ppm (e.g., 5.75 to 5.87 ppm); 5.85 to 6.10 ppm (e.g., 5.90 to 6.05 ppm). In one embodiment, the structural moiety is associated with a proton of peak 1 of FIG. 1, a proton of peak 2 of FIG. 1, a proton of peak 3 of FIG. 1, a proton of peak 4 of FIG. 1, a proton of peak 5 of FIG. 1, a proton of peak 6 of FIG. 1, a proton of peak 7 of FIG. 1, a proton of peak 8 of FIG. 1.

In some embodiments, an enoxaparin preparation is analyzed by $^1H$ NMR to provide the total glucosamine content (TG). In some embodiments, an enoxaparin preparation is analyzed by $^1H$ NMR to provide the total uronic acid content (TU). In some embodiments, an enoxaparin preparation is analyzed by $^1H$ NMR to provide the relative percentage of glucosamine residues (H) or uronic acid residues in a sample (I/G).

In another embodiment, a method described herein can be used to detect the presence or amount of a structural moiety provided in Table 2 such as a glucosamine residue (e.g., an N-sulfated glucosamine, a 3-O, N-Sulfated glucosamine, or an N-Acetyl glucosamine) or a uronate residue (e.g., a 2-O Sulfated uronate residue, an unsulfated uronate residue, or an IdoA/GlcA).

In some embodiments, the preparation includes one or more of the structures provided in Table 2 below.

TABLE 2

| Monosaccharide Signatures | | Integration range A* (mol %)** | Integration range B* (mol %)** | Integration range C* (mol %)** | Integration range D* (mol %)** |
|---|---|---|---|---|---|
| Glucosamine Residues | N-sulfated | 80-82 | 75-85 | 72.4-89.8 | 72-90 |
| | 3-O, N-Sulfated | 5-6 | 4.5-6.5 | 4.2-6.7 | 4-7 |
| | N-Acetyl | 12.5-13.5 | 12-14 | 11.3-15.9 | 11-16 |
| Uronates Residues | 2-O Sulfated | 60.5-62.5 | 57-65 | 54.6-69.8 | 54-70 |
| | Unsulfated | 37.5-39.5 | 35-42 | 32.9-43.2 | 32-44 |
| | IdoA/GlcA | 2.0-2.5 | 1.9-2.3 | 1.8-2.5 | 1.5-3.5 |

*The ranges provided in the table above are inclusive of the endpoints provided
**Mole % for each type of glucosamine or uronate residue is calculated relative to the total glucosamine content or uronic acid content, respectively.

In some embodiments, the amount of subject entity is determined and, e.g., evaluated to determine if it is present in a preselected amount or range such as described in Table 2 above. This can be done by comparing with a range of reference values for that subject entity. E.g., an amount for one or more or all of the structural moieties evaluated, e.g., for presence or to determine if the subject entity is present in a range indicated in Table 2.

In one embodiment, the method includes normalizing all proton signals with respect to a reference signal. For example, the quantity of the reference value can correspond to the quantity of total heparin in the preparation, e.g., total chains of enoxaparin in the preparation. The reference value can be the integral of a proton signal associated with one or more structural moieties in the heparin preparation. In one embodiment, the reference signal is the integral of one signal in the spectrum, e.g., the integrated intensity of the H2 proton of N-sulfated glucosamine. In another embodiment, the reference signal is the sum of the integrals of multiple peaks, e.g., the sum of the integrated intensities of the H4 signals of both ΔU and $ΔU_{2S}$.

In one embodiment, a percentage of the structural moiety, e.g., the total percentage of the structural moieties, in the preparation has been determined, e.g., as measured by mole %, and preferably the method includes determining or confirming that the moiety is in that range.

In one embodiment, the method further includes determining if a proton associated with one or more contaminant, e.g., one or more non-heparin saccharide contaminant, is present in the preparation. In one embodiment, the method further includes determining if a proton associated with dermatan sulfate is present in the preparation. In one embodiment, the presence of a non-heparin saccharide contaminant such as dermatan sulfate can be determined, e.g., by a chemical shift of peak 1 of FIG. 1 by about 0.01 to about 0.1, e.g., about 0.03 to about 0.08 and/or by a split in peak 1 of FIG. 1. In one embodiment, the method includes determining the amount of a contaminant in preparation, e.g., as compared to a reference standard, e.g., a reference standard of less than 3%, 2%, 1%, 0.5%, 0.1%.

In one embodiment, the method includes determining if one or more of the compounds provided in Table 2 is present, and, e.g., present in a range specified herein e.g., in Table 2. The ranges A, B, C and D, for a given structure are shown in Table 2 but other ranges can be used as well. E.g., ranges can constructed from a lower endpoint of one range, e.g., B, for a given building block, can be combined with the upper endpoint of another range, e.g., C, for the given building block, to give a range.

In one embodiment, the method includes determining the identity, presence, and/or quantity of at least two or more (e.g., 2, 3, 4, 5, or 6) of the structures of Table 2, in the preparation. In one embodiment, the method includes determining if the subject entities are present in a range disclosed herein, e.g., in Table 2. In one embodiment, the method includes comparing the determination to a reference standard, e.g., the presence of structures Table 2 and/or the quantity of structures of Table 2. In a preferred embodiment, the sample is evaluated for the presence of each of the structures in Table 2.

In a preferred embodiment, the sample is evaluated for the presence of each of the structures in Table 2.

In a preferred embodiment, one or more structures from a subset of the structures in Table 2 are evaluated.

In one embodiment, the method includes $^{13}$C 1D NMR to quantify the amount of signature $^{13}$C peaks with respect to a reference signal. For example, the quantity of the reference value can correspond to the quantity of total heparin in the preparation, e.g., total chains of enoxaparin in the preparation. The reference value can be the integral of a $^{13}$C signal associated with one or more structural moieties in the heparin preparation. In one embodiment, the reference signal is the integral of one signal in the spectrum. In another embodiment, the reference signal is the sum of the integrals of multiple peaks.

In a preferred embodiment, the sample is evaluated with 2D NMR, e.g., a heteronuclear experiment using $^1$H and $^{13}$C NMR performed on a sample of an enoxaparin preparation, e.g., an unmodified sample of enoxaparin. In a preferred embodiment, the method includes: providing an enoxaparin preparation; and subjecting the enoxaparin preparation to analysis with 2D $^1$H and $^{13}$C NMR, and optionally, evaluating the presence, distribution, or amount, of a selected subject entity, e.g., a structure or species e.g., a selected structure in a sample.

In one embodiment, one or more of nuclear Overhauser effect spectroscopy (NOESY), rotating frame Overhauser effect spectroscopy (ROESY), correlation spectroscopy (COSY), incredible natural abundance double quantum transfer experiment (INADEQUATE) or total correlated spectroscopy (TOCSY) can be used. In one embodiment, 2D NMR is used and the first proton is quantified by integrating the crosspeak and the corresponding diagonal peak.

In a preferred embodiment, a structure is evaluated using, 2D NMR, e.g., $^1$H/$^{13}$C NMR, where one or more acidic hydrogens have been exchanged with deuterium, e.g., a sample of a polysaccharide mixture is exchanged with $D_2O$, lyophilized over night, and redissolved in $D_2O$.

In some embodiments, the 2D NMR spectrum is acquired using carbon decoupling during acquisition.

In some embodiments, the 2D NMR spectrum is acquired with a polarization transfer delay of from about 2.3 ms to about 3.9 ms, e.g. about 3.2 ms, with $^1J_{CH}$ scalar couplings of from about 130 to about 210 Hz, e.g., about 155 Hz.

The data is generally then processed and cross peaks are integrated, for example, using Bruker's XWINNMR or Topspin software. In a preferred embodiment, one or more of the following techniques is used during processing: linear prediction, zero filling, Fourier transformation, and baseline correction. In one embodiment, a non-linear transformation, e.g., Maximum Entropy Reconstuction or the Filter Diagonalization Method, is used instead of Fourier transformation. In one embodiment, a non-linear transformation is used on a sum of the experimental data and a set of synthetic signals; the synthetic signals are used to compensate for the non-linear response. Peaks are generally assigned using published chemical shifts and/or model compounds to assign chemical shifts.

In one embodiment, the structure can be naturally associated with a starting material, e.g., unfractionated heparin. In another embodiment, the structure can be a structure not naturally associated with a starting material, e.g., a structure not naturally present in a chain of unfractionated heparin. For example, a "modified structure" can be, e.g., a structure resulting from a method used to make a LMWH sample. In one embodiment, the preparation is an enoxaparin preparation and the modified structure can be one or more of: an epoxide, an mannosamine, a uronate at the reducing end, 1,6an Glc$_{NS}$, 1,6an Man$_{NS}$, and a galacturonic acid. In one embodiment, the method includes determining if one or more reducing end and/or non-reducing end monosaccharide structure is present in the sample. In one embodiment, one or more of the protons identified is associated with an epimerized state of a uronic acid, e.g., iduronic acid and/or glucuronic acid, e.g., a 2-O sulfated and/or unsulfated iduronic acid, glucuronic acid or combinations thereof. In one embodiment, one or more of the protons identified is associated with a uronic acid having a Δ4,5 double bond, e.g., a sulfated and/or non-sulfated uronic acid having a Δ4,5 double bond. In one embodiment, one or more protons identified are associated with a glucosamine, e.g., a glucosamine having one or more of the following properties: N-acetylated, N-sulfated, and 3-O sulfated. In one embodiment, one or more protons identified are associated with a mannosamine. In one embodiment, one or more protons are associated with an epoxide. In another embodiment, the method identifies a glycosidic linkage associated with a monosaccharide structure, e.g., a linkage between a hexosamine and an uronic acid. In another embodiment, the method can be used to evaluate a structure adjacent to a reducing end structure, e.g., to determine the structure adjacent to a reducing end structure.

In one embodiment, the method includes determining the presence, distribution or amount of a structure provided in Tables 3 or 4.

TABLE 3

| Monosaccharide | Percentage Composition Range A* | Percentage Composition Range B | Percentage Composition Range C |
|---|---|---|---|
| Hexosamine Residues | | | |
| Total N-sulfated hesoxamine ($H_{NS}$) | 84-88 | 80-90 | 77-95 |
| $H_{NS}$-G | 10.7-11.2 | 10.5-11.5 | 9.5-12.0 |
| $H_{NS}$-I | 7.0-8.0 | 6.7-8.0 | 6.3-8.2 |
| 1,6 An Man | 2.3-2.7 | 2.2-2.8 | 2.1-2.9 |
| 1,6 An Glc | 2.7-2.8 | 2.6-3.0 | 2.5-3.1 |
| Total 1,6 anhydro | 5.2-5.4 | 5.0-5.6 | 4.6-5.8 |
| 3-O-sulfated glucosamine ($H_{NS,3S,6S}$) | 3.9-4.4 | 3.7-4.5 | 3.5-4.6 |
| N-acetyl glucosamine ($H_{NAc}$) | 9.0-10.0 | 8.9-10.2 | 8.8-10.8 |
| 6-O-sulfated glucosamine ($H_{6S}$) | 83-88 | 78-90 | 75-92 |
| Uronic acid residues | | | |
| 2-O-sulfated uronic acid | 74-76 | 71-80 | 67-83 |
| $I_{2S,red}$ | 0.9-1.2 | 0.9-1.3 | 0.8-1.4 |
| $G_{2S}$ | 2.6-3.0 | 2.5-3.1 | 2.5-3.3 |
| Non-sulfated uronic acid | 24-26 | 23-27 | 22-28 |
| 1-$H_{NS/Ac,6S}$ | 5.3-6.4 | 5.0-6.5 | 4.7-6.5 |
| I-$H_{NS,Ac}$ | 0.90-1.40 | 0.8-1.50 | 0.8-1.55 |
| G-$H_{NS}$ | 12.5-13.5 | 11.8-13.7 | 11.3-13.9 |
| G-$H_{NAc}$ | 3.10-4.40 | 3.00-4.60 | 3.00-4.85 |
| Other residues | | | |
| Epoxide | 0.7-0.9 | 0.65-0.95 | 0.6-1.0 |

*The ranges provided in the table above are inclusive of the endpoints provided

In some embodiments, the amount of subject entity is determined and the evaluated to determine if it is present in a preselected amount or range, e.g., an amount or range described herein, e.g., in Table 3 above. This can be done by comparing with a range of reference values for that subject entity. E.g., an amount for one or more or all of the structures evaluated, e.g., for presence or to determine if the subject entity is present in a range indicated in Table 3.

In one embodiment, a method described herein can be used to detect the presence or relative amount of a structure provided in Table 3 such as a hexosamine residue, for example, total N-sulfated hesoxamine ($H_{NS}$) such as $H_{NS}$-G, $H_{NS}$-I, 1,6 An Man, and 1,6 An Glc, total 1,6 anhydro moieties, 3-O-sulfated glucosamine ($H_{NS,3S,6S}$), N-acetyl glucosamine ($H_{NAc}$), or 6-O-sulfated glucosamine ($H_{6S}$); or a uronic acid residue, for example, a 2-O-sulfated uronic acid such as $I_{2S,red}$, or $G_{2S}$, or a non-sulfated uronic acid such as 1-$H_{NS/Ac,6S}$, I-$H_{NS/Ac}$, G-$H_{NS}$, or G-$H_{NAc}$.

In one embodiment, the method includes determining if one or more of the compounds provided in Table 3 is present, and, e.g., present in a range specified herein e.g., in Table 3. The ranges A, B, C and D, for a given structure are shown in Table 3 but other ranges can be used as well. E.g., ranges can constructed from a lower endpoint of one range, e.g., B, for a given building block, can be combined with the upper endpoint of another range, e.g., C, for the given building block, to give a range.

In one embodiment, the method includes determining the identity, presence, and/or quantity of at least two or more (e.g., 2, 3, 4, 5, 6, 7, 8, 9, 10, 11, 12, 13, 14, 15, 16, 17 or 18) of the structures of Table 3, in the preparation. In one embodiment, the method includes determining if the subject entities are present in a range disclosed herein, e.g., in Table 3. In one embodiment, the method includes comparing the determination to a reference standard, e.g., the presence of structures Table 3 and/or the quantity of structures of Table 3.

In a preferred embodiment, the sample is evaluated for the presence of each of the structures in Table 3.

In a preferred embodiment, one or more structures from a subset of the structures in Table 4 are evaluated, e.g.: ΔU, ΔU$_2$s, 1,6 an Glc, 1,6 an Man, epoxide, 3-O-sulfated glucosamine, reducing-end 2-O-sulfated iduronic acid, and reducing-end mannosamine.

TABLE 4

| Peak | Chemical Shift range (ppm) | Chemical Shift (ppm)* | Assignment |
|---|---|---|---|
| P1 | 3.31-3.21/ 60.9-60.1 | 3.26# ± 0.05/60.5§ ± 0.4 | H-2/C-2 of N-sulfated glucosamine ($H_{NS,6X}$) |
| P2 | 3.48-3.38/ 59.0-59.8 | 3.43# ± 0.05/59.4§ ± 0.4 | H-2/C-2 of N-sulfated, 3-O-sulfated glucosamine ($H_{NS,3S,6X}$) |
| P3 | | 3.90#/56.5§ | H-2/C-2 of N-acetyl glucosamine ($H_{NAc,6X}$) |
| P4 | | 3.18#/58.5§ | H-2/C-2 of 1,6-anhydro-N-sulfated glucosamine (1,6an$H_{NS}$) |
| P5 | | 3.45#/54.9§ | H-2/C-2 of 1,6-anhydro-N-sulfated mannosamine (1,6anMan$_{NS}$) |
| P6 | | 3.58#/60.2§ | H-2/C-2 of N-sulfated mannosamine α redox (Man$_{NS,6X}$αred) |
| P7 | | 3.04#/63.7§ | H-2/C-2 of N-sulfated glucosamine β redox ($H_{NS,6X}$βred) |
| P8 | | 3.80#/62.4§ | H-6,6'/C-6 of N-sulfated/acetylated glucosamine ($H_{NS/NAc,6OH}$) |
| P9 | | 3.75#/67.4§ | H-6/C-6 of 1,6-anhydro-N-sulfated mannosamine (1,6anMan$_{NS}$) |
| P10 | | 3.77#/68.0§ | H-6/C-6 of 1,6-anhydro-N-sulfated glucosamine (1,6an$H_{NS}$) |
| P11 | | 4.5-4.2#/69.9-68.4§ | H-6,6'/C-6 of N-sulfated/acetylated, 6-O-sulfated glucosamine ($H_{NS,NAc,6S}$) (integrates as 2 protons) |
| P12 | | 5.61#/104.2§ | H-1/C-1 of 1,6-anhydro-N-sulfated glucosamine (1,6an$H_{NS}$) |
| P13 | | 5.55#/103.7§ | H-1/C-1 of 1,6-anhydro-N-sulfated mannosamine (1,6anMan$_{NS}$) |
| P14 | | 5.55#/100.5§ | H1/C1 of N-sulfated glucosamine linked to glucuronic acid ($H_{NS,6X}$-G) |
| P15 | | 5.49#/100.0§ | H-1/C-1 of ΔUAp2S residue (ΔU$_{2S}$) |
| P16 | | 5.50#/98.9§ | H-1/C-1 of N-sulfated, 3-O-sulfated glucosamine ($H_{NS,3S,6X}$) |
| P17 | | 5.32#/98.3§ | H-1/C-1 of N-sulfated glucosamine linked to iduronic acid ($H_{NS,6X}$-I) |
| P18 | | 5.4-5.3#/100.4-98.8§ | H-1/C-1 of N-sulfated glucosamine linked to 2-O-sulfated iduronic acid ($H_{NS,6X}$-I$_{2S}$) + N-acetyl glucosamine ($H_{NAc,6X}$) |
| P19 | | 5.40#/97.3§ | H-1/C1 2, 3 epoxide |
| P20 | | 5.38#/95.6§ | H-1/C-1 of N-sulfated mannosamine α redox (Man$_{NS,6X}$αred) |
| P21 | | 5.40#/95.5§ | H-1/C-1 of 2-O-sulfated iduronic acid redox (I$_{2S}$red) |

TABLE 4-continued

| Peak | Chemical Shift range (ppm) | Chemical Shift (ppm)* | Assignment |
|---|---|---|---|
| P22 | | 5.43#/93.8§ | H-1/C-1 of N-sulfated glucosamine α redox ($H_{NS,6X}$αred) |
| P23 | | 4.69#/98.5§ | H-1/C-1 of N-sulfated glucosamine β redox ($H_{NS,6X}$βred) |
| P24 | | 5.32#/101.7§ | H-1/C-1 of 2-O-sulfated iduronic acid liked to 1,6anMan$_{NS}$ ($I_{2S}$-1,6anMan$_{Ns}$) |
| P25 | | 5.2-5.1#/102.5-101.7§ | H-1/C-1 of 2-O-sulfated iduronic acid ($I_{2S}$) |
| P26 | | 5.14#/103.8§ | H-1/C-1 of ΔUAp2-OH residue (ΔU) |
| P27 | | 4.98#/104.8§ | H-1/C-1 of iduronic acid linked to N-sulfated, 6-O-sulfated glucosamine (I-$H_{NS,6S}$) |
| P28 | | 4.92#/104.6§ | H-1/C-1 of iduronic acid linked to N-sulfated, 6-OH glucosamine (I-$H_{NS,6OH}$) |
| P29 | | 4.73#/102.8§ | H-1/C-1 of 2-O-sulfated glucuronic acid ($G_{2S}$) |
| P30 | | 4.58#/104.7§ | H-1/C-1 of glucuronic acid linked to N-sulfated glucosamine (G-$H_{NS,6X}$) |
| P31 | | 4.59#/103.7§ | H-1/C-1 of glucuronic acid linked to N-sulfated, 3-O-sulfated glucosamine (G-$H_{NS,3S,6X}$) |
| P32 | | 4.48#/105.0§ | H-1/C-1 of glucuronic acid linked to N-acetyl glucosamine (G-$H_{NAc,6X}$) |
| P33 | | 4.51#/104.1§ | H1/C1 of galacturonic of the linkage region (LR) |
| P34 | | 4.43#/105.6§ | H1/C1 of xylose of the linkage region (LR) |
| P35 | | 4.64#/106.6§ | H1/C1 of galacturonic acid + galactose of the linkage region (integration of two protons) |

*Peak positions are the approximate center of the specified peaks.
Peak positions may shift of ±0.05 ppm in the proton dimension
§Peak positions may shift of ±0.4 ppm in the carbon dimension In one embodiment, the structural moiety is associated with a proton/carbon of P1, table 4; a proton/carbon of P2, table 4; a proton/carbon of P3, table 4; a proton/carbon of P4, table 4; a proton/carbon of P5, table 4; a proton/carbon of P6, table 4; a proton/carbon of P7, table 4; a proton/carbon of P8, table 4; a proton/carbon of P9, table 4; a proton/carbon of P10, table 4; a proton/carbon of P11, table 4; a proton/carbon of P12, table 4; a proton/carbon of P13, table 4; a proton/carbon of P14, table 4; a proton/carbon of P15, table 4; a proton/carbon of P16, table 4; a proton/carbon of P17, table 4; a proton/carbon of P18, table 4; a proton/carbon of P19, table 4; a proton/carbon of P20, table 4; a proton/carbon of P21, table 4; a proton/carbon of P22, table 4; a proton/carbon of P23, table 4; a proton/carbon of P24, table 4; a proton/carbon of P25, table 4; a proton/carbon of P26, table 4; a proton/carbon of P27, table 4; a proton/carbon of P28, table 4; a proton/carbon of P29, table 4; a proton/carbon of P30, table 4; a proton/carbon of P31, table 4; a proton/carbon of P32, table 4; a proton/carbon of P33, table 4; a proton/carbon of P34, table 4; pr a proton/carbon of P351, table 4.

In one aspect, the invention features a method of evaluating or processing a LMWH heparin preparation, e.g., an enoxaparin preparation, that includes making a determination about the LMWH preparation, e.g., an enoxaparin preparation, based upon a method or analysis described herein. In one embodiment, the method further includes classifying, selecting, accepting or discarding, releasing or withholding, processing into drug product, shipping, moving to a new location, formulating, labeling, packaging, releasing into commerce, selling or offering to sell, the preparation based, e.g., on the analysis. Thus, in a preferred embodiment the party making the evaluation does not practice the method or analysis described herein but merely relies on results which are obtained by a method described herein.

Methods described herein can be used to evaluate a LMWH preparation by evaluating one or more subject entities revealed by 1D NMR or present in Table 1 or Table 2, and/or by evaluating one or more subject entities revealed by 2D NMR or present in Tables 3 or 4. Thus, methods described herein can be combined to provide analysis of a LMWH, e.g., enoxaparin.

Accordingly, in one aspect, the invention provides, a method of evaluating or processing a polysaccharide mixture, e.g., a LMWH, e.g., an enoxaparin preparation.

The method includes:

providing an evaluation of a parameter related to a subject entity from Table 1, Table 2 or resolved by 1D NMR;

providing an evaluation of a parameter related to a subject entity from Table 3, Table 4, or resolved by 2D NMR; and, optionally, providing a determination of whether a value (e.g., a value correlated to presence or absence, distribution or amount) determined for the parameter for one or both the Table 1 and/or Table 2 subject entity and the Tables 3 or 4 subject entity each meets a preselected criterion for that subject entity, e.g., is present or is present within a preselected range, thereby evaluating or processing the mixture.

In a preferred embodiment, the method includes providing a comparison of the value determined for a parameter with a reference value or values, to thereby evaluate the sample. In preferred embodiments, the comparison includes determining if the test value has a preselected relationship with the reference value, e.g., determining if it meets the reference value.

Combination methods can incorporate any of the features or steps described herein for other methods. E.g., in preferred embodiments, the test value, or an indication of whether the preselected criterion is met, can be memorialized, e.g., in a computer readable record. By further example, a combination method can include embodiments wherein a decision or step is taken, e.g., the sample is classified, selected, accepted or discarded, released or withheld, processed into a drug product, shipped, moved to a new location, formulated, labeled, packaged, released into commerce, or sold or offered for sale, depending on whether the preselected criterion is met. E.g., based on the result of the determination or whether one or more subject entities is present, or upon comparison to a reference standard, the batch from which the sample is taken can be processed, e.g., ΔU, ΔU$_2$s, 1,6 an Glc, 1,6 an Man, epoxide, 3-O-sulfated glucosamine, reducing-end 2-O-sulfated iduronic acid, and reducing-end mannosamine.

In one aspect, the invention features a method of analyzing a process, e.g., a manufacturing process, of an enoxaparin, e.g., an enoxaparin made by a selected process. The method includes: providing an enoxaparin preparation; analyzing the enoxaparin preparation using a method described herein, e.g., to identify one or more structure, e.g., one or more structure disclosed herein, thereby allowing analysis, e.g., qualitative analysis, of the one or more structure in the enoxaparin preparation. In one embodiment, the method further includes comparing the presence or size distribution of the one or more structure with a reference value, to thereby analyze the manufacturing process.

In one embodiment, the method further includes maintaining the manufacturing process based, at least in part, upon the analysis. In one embodiment, the method further includes altering the manufacturing process based, at least in part, upon the analysis.

In a preferred embodiment, the method includes evaluating a process, e.g., manufacturing process, of an enoxaparin, e.g., an enoxaparin made by a selected process, that includes making a determination about the process, e.g., manufacturing process, or enoxaparin, e.g., enoxaparin made by a selected process, based upon a method or analysis described herein. In one embodiment, the method further includes maintaining or altering the manufacturing process based, at least in part, upon the method or analysis. Thus, in a preferred embodiment, the party making the evaluation does not practice the method or analysis described herein but merely relies on results which are obtained by a method or analysis described herein.

In a preferred embodiment, the method includes comparing two or more heparin preparations, e.g., two or more enoxaparin preparations, e.g., in a method of monitoring or controlling batch-to-batch variation or to compare a preparation to a reference standard. This embodiment includes: providing a first heparin preparation; providing the presence or amount of one or more structure, e.g., one or more structure described herein, in the first sample; optionally, providing a second heparin preparation; providing the presence or amount of a structure in the second preparation; and comparing the presence or size distribution of the one or more structure of the first heparin preparation with the one or more structure of the second heparin preparation. In one embodiment, the one or more structure is analyzed by a method described herein.

In one embodiment, the method can further include making a decision, e.g., to classify, select, accept or discard, release or withhold, process into drug product, ship, move to a different location, formulate, label, package, release into commerce, sell of offer to sell the preparation, based, at least in part, upon the determination, and optionally, carrying out the decision.

In one aspect, the invention features a method of making a batch of enoxaparin having a preselected property, e.g., meeting a release specification, label requirement, or compendial requirement. The method includes:

providing a test enoxaparin preparation;

analyzing the test enoxaparin preparation according to a method described herein;

determining if the test enoxaparin preparation includes one or more of the structures in Table 1, 2, 3 or 4 and selecting the test enoxaparin preparation to make enoxaparin, thereby making a batch of enoxaparin.

In one aspect, the invention features a method of predicting or ensuring that a batch of enoxaparin will have a preselected property, e.g., that it will meet a release specification, label requirement, or compendial requirement. The method includes:

providing a test enoxaparin preparation;

analyzing the test enoxaparin preparation according to a method described herein;

wherein satisfaction of the preselected reference, e.g., one or more reference disclosed herein, by the test enoxaparin preparation, is predictive of or ensures that a batch of enoxaparin made from the test enoxaparin preparation will have a preselected property, e.g., it will meet a release specification, label requirement, or compendial requirement, e.g., a property described herein.

In one aspect, the invention features a method of making one or more batches of a polysaccharide preparation, e.g., an enoxaparin preparation, wherein the glycoprofile (e.g., one or more structural property, e.g., the presence or amount of a structure described herein) of the batches has some preselected relationship with a reference standard. Preferably, evaluation of the glycoprofile, e.g., the presence of a structure, is made by a method described herein. In some embodiments, the method further includes classifying or selecting one or more batches having a structural property that corresponds with one or more of the reference structures, e.g., the structures described herein.

In another aspect, the invention features multiple batches of a polysaccharide preparation, e.g., an unfractionated heparin preparation or enoxaparin preparation, wherein the glycoprofile (e.g., determined by a method described herein) for each batch has a pre-selected desired glycoprofile, e.g., a glycoprofile for one or more, preferably all, of the structures described herein. In some embodiments, the method includes determining one or more structural signature (e.g., one or more structural moiety and/or chain) of one or more batches of a product, and selecting a batch as a result of the determination. In some embodiments, the method can also include comparing the results of the determination to preselected values, e.g., a reference standard. In other embodiments, the method can further include adjusting the dose of the batch to be administered, e.g., based on the result of the determination of the structural signature. Preferably, evaluation of the value, e.g., the presence of one or more structure and/or chain, is made by a method described herein.

In another aspect, the invention features a method of determining a reference value for a polysaccharide composition, e.g., an enoxaparin preparation, and determining the presence of one or more structure described herein including those provided in Table 1, 2, 3, or 4. Preferably, evaluation of the value, e.g., the presence or size distribution of the one or more structure, is made by a method described herein.

In another aspect, the invention features a method for determining bioequivalence. The method includes some or all of the following: providing or determining a value for the presence or size distribution of one or more subject entity, e.g., one or more structure described herein, in a first heparin preparation, e.g. an enoxaparin preparation; providing or determining the bioavailability of the preparation; providing a reference value, e.g., by providing or determining presence or amount of one or more structure, e.g., one or more structure described herein, in a second heparin preparation, e.g., an enoxaparin preparation, and comparing the presence or amount of one or more structure of the first preparation and/or the reference value, e.g., a second heparin preparation. In some embodiments, the reference value can include one or more of the structures described herein. Preferably, evaluation of the one or more structure is made by a method described herein.

In some embodiments, the method further comprises monitoring for presence, tissue distribution, spatial distribution, temporal distribution or retention time, in a cell or a subject, e.g., an experimental animal. In some embodiments, the method includes determining the presence or amount of one or more structure described herein of one or more batches of a product. In some embodiments, the method further includes selecting a batch as a result of the determination. In some embodiments, the method further includes comparing the results of the determination to preselected values, e.g., a reference standard.

In another aspect, the invention provides a method for determining the safety or suitability of a heparin, e.g., a LMWH, preferably an enoxaparin preparation for use in a particular indication. The method includes some or all, typically all, of the following: determining the presence or amount of one or more structure e.g., one or more structure described herein, in the heparin; providing a reference value or sample; determining if the heparin is acceptable, e.g., by comparing a value for the presence or amount of one or more structure and of the heparin with the reference value or with a value determined from the sample. For example, when the heparin is enoxaparin, one or more of the structures described herein can be used as a reference value. When a preselected index of similarity is met, the heparin can be determined to be safe or suitable. In some embodiments, the reference sample is associated with one or more undesired effects. In some embodiments, the reference sample is associated with one or more desired effects. Preferably, evaluation of the presence or amount of the one or more structure, e.g., one or more structure described herein, in the heparin is made by a method described herein.

In another aspect, the invention features a method of one or more of providing: a report to a report receiving entity; evaluating a sample of enoxaparin for compliance with a reference standard, e.g., an FDA requirement; seeking indication from another party that an enoxaparin sample meets some predefined requirement; or submitting information about an enoxaparin sample to another party. Exemplary receiving entities or other parties include a government, e.g., the U.S. federal government, e.g., a government agency, e.g., the FDA.

The method includes one or more (and preferably all) of the following:

performing one or more steps in making and/or testing a batch of enoxaparin in a first country, preferably the US;

sending at least an aliquot of the sample outside the first country, e.g., sending it outside the United States, to a second country;

preparing, or receiving, a report which includes data about the structure of the enoxaparin sample, e.g., data related to a subject entity, e.g., a structure described herein, e.g., data generated by one or more of the methods described herein;

providing said report to a report recipient entity.

In a preferred embodiment, the report receiving entity can determine if a predetermined requirement or reference value is met by said data and optionally, a response from the report receiving entity is received, e.g., by a manufacturer, distributor or seller of enoxaparin. In a preferred embodiment, upon receipt of approval from said report recipient entity, enoxaparin from said batch is selected, packaged, or placed into commerce.

In one aspect, the invention features a method of evaluating a sample of enoxaparin that includes receiving data with regard to the presence of a subject entity, e.g., a structure described herein in an enoxaparin sample, e.g., wherein the data was prepared by one or more methods described herein; providing a record which includes said data and optionally includes an identifier for a batch of enoxaparin; submitting said record to a decision-maker, e.g., a government agency, e.g., the FDA; optionally, receiving a communication from said decision maker; optionally, deciding whether to release market the batch of Lovenox or enoxaparin based on the communication from the decision maker. In one embodiment, the method further includes releasing the sample.

Any of the methods described herein can further include determining and/or providing an analysis regarding one or more biological activity of the preparation or sample. For example, the biological activity can be one or more of anti-Xa activity, anti-IIa activity, molecular weight distribution and average molecular weight. The methods can further include comparing any of anti-Xa activity, anti-IIa activity, molecular weight distribution and average molecular weight to a reference standard for enoxaparin. In one embodiment, the reference standard for anti-Xa activity is about 100 IU/mg; the reference standard for anti-IIa activity is about 30 IU/mg; the reference standard for molecular weight distribution is 20% are <2000 Da species, greater than or equal to 68% are 2000-8000 Da species, and less than or equal to 18% are >8000 Da species; the reference standard for the average molecular weight is about 4500 Da.

A "polysaccharide" as used herein is a polymer composed of monosaccharides linked to one another. In many polysaccharides, the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide).

A polysaccharide according to the invention can be a mixed population of polysaccharides, e.g., a heparin preparation e.g., synthetic heparin preparation, an unfractionated heparin preparation or LMWH preparation. As used herein, a "mixed population of polysaccharides" is a polydisperse mixture of polysaccharides. The term "polydisperse" or "polydispersity" refers to the weight average molecular weight of a composition (Mw) divided by the number average molecular weight (Mn). The polydispersity of unfractionated heparin and various LMWHs are known, as are methods for determining polydispersity. Compositions with polydispersity near 1 are more homogeneous, containing fewer different polysaccharides. As an example, a preparation of unfractionated heparin, which contains a wide variety of polysaccharides of differing lengths and compositions, has a polydispersity of about 1.5 to 2.0.

The term "enoxaparin preparation" as used herein refers to both enoxaparin drug substance preparations and enoxaparin drug product preparations. The term "drug product preparation" refers to a polysaccharide preparation having the purity required for and being formulated for pharmaceutical use. The term "drug substance preparation" refers to a preparation having the polysaccharide constituents for pharmaceutical use but is not necessarily in its final formulation and/or comprises one or more non-product contaminant (e.g., one or more inorganic product such as sulfate, chloride, acetate and phosphates, protein contaminant, process by-product such as benzyl alcohol and benethonium).

The term "unfractionated heparin (UFH)" as used herein, is heparin purified from porcine intestinal mucosa that can be used as a starting material in the process to form enoxaparin.

Complex polysaccharide drug products can be isolated or derived from natural sources and are complex mixtures of polysaccharide chains that differ from one another both in terms of size and chemical sequence that comprises each polysaccharide chain. Chain sequence differences can arise both from differences intrinsic to the cell and tissue-specific biosynthesis pathway by which these complex polysaccharides are made as well as from differences that arise as a function of the process of isolating or preparing polysaccharide substances from natural sources. For example, the LMWHs are derived from unfractionated heparin (UFH) primarily through chemical or enzymatic depolymerization of the polysaccharide chains. Thus, different LMWHs can be made by various depolymerization processes. A process used to make a LMWH can cause one or more unique structural modifications to the polysaccharide chains of the polysaccharide drug, such as heparin. For example, esterification of the carboxylate functional group on the uronic acid followed by β-elimination results in the formation of a Δ4,5 double bond on the non-reducing end as well as the formation of some chains having 1,6-anhydro derivatives. In addition, differences can arise in LMWH preparations due to variation in the starting material. As a result of these structural differences, different LMWHs can have distinct pharmacological and/or structural profiles.

The details of one or more embodiments of the invention are set forth in the accompanying drawings and the description below. Other features, objects, and advantages of the invention will be apparent from the description and drawings, and from the claims.

DESCRIPTION OF DRAWINGS

The drawings are first briefly described.

FIG. 2a depicts a sample with detectable amount of dermatan sulfate, and FIG. 2b depicts a sample with no detectable amount of dermatan sulfate.

DETAILED DESCRIPTION

Reference Values and Standards

Figure 1:
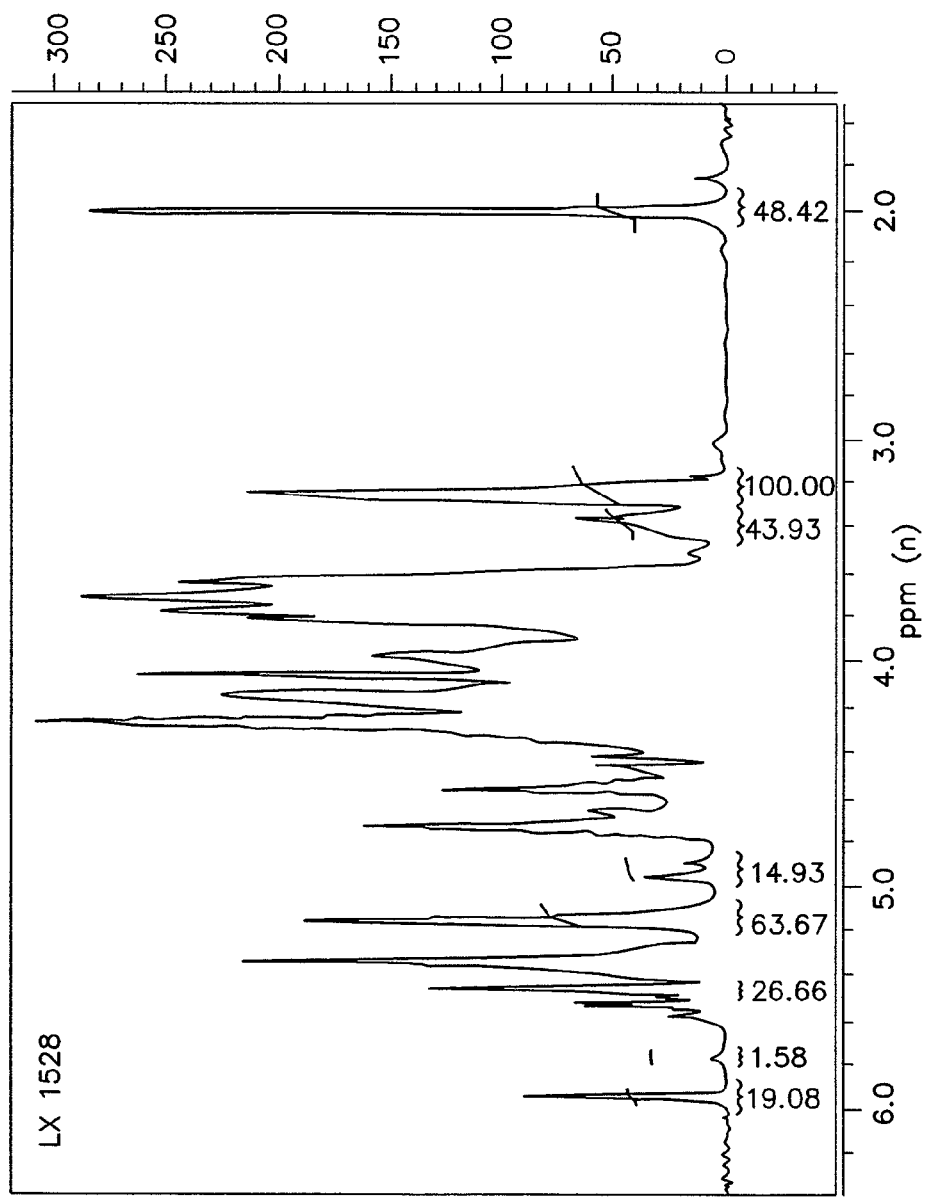
FIG. 1 is an $^1$H NMR spectrum of a LOVENOX® preparation, corresponding to the portion spanning from about 1.6 ppm to about 6.4 ppm.

A reference value, by way of example, can be a value determined from a reference sample (e.g., a commercially available sample or a sample from previous production). E.g., a reference value can be a value for the presence of a subject entity in a sample, e.g., a reference sample. The reference value can be numerical or non-numerical. E.g., it can be a qualitative value, e.g., yes or no, or present or not present at a preselected level of detection, or graphic or pictorial. The reference value can also be values for the presence of more than one subject entity in a sample. For example, the reference value can correspond to a peak in an NMR spectrum corresponding to a structure present in enoxaparin when analyzed by NMR, e.g., a 1D NMR or 2D NMR method described herein. The reference value can also be a release standard (a release standard is a standard which should be met to allow commercial sale of a product) or production standard, e.g., a standard which is imposed, e.g., by a party, e.g., the FDA, on a LMWH, e.g., enoxaparin.

The reference standard can be derived from any of a number of sources. The reference standard can be one which was set or provided by (either solely or in conjunction with another party, e.g., a regulatory agency, e.g., the FDA) the manufacturer of the drug or practitioner of a process to make the drug. The reference standard can be one which was set or provided by (either solely or in conjunction with another party, e.g., a regulatory agency, e.g., the FDA) a party other than the party manufacturing a drug and practicing a method disclosed herein, e.g., another party which manufactures the drug or practices a process to make the drug. The reference standard can be one which was set or provided by (either solely or in conjunction with another party) a regulatory agency, e.g., the FDA, to the manufacturer of the drug or practitioner of the process to make the drug, or to another party licensed to market the drug. E.g., the reference standard can be a production, release, or product standard required by the FDA. In preferred embodiments, a reference standard is a standard required of a pioneer drug (e.g., a drug marketed under an approved NDA) or a generic drug (e.g., a drug marketed or submitted for approval under an ANDA).

The reference standard can be one which was set or provided by Aventis Pharma SA, its fully owned subsidiaries, its successors and assigns or agents, either solely or in conjunction with another party, e.g., a regulatory agency, e.g., the FDA, for production or release of a LMWH, e.g., enoxaparin.

The reference standard can be one which was set or provided by Momenta Pharmaceuticals, Inc., its fully owned subsidiaries, its successors and assigns or agents, either solely or in conjunction with another party, e.g., a regulatory agency, e.g., the FDA, for production or release of a LMWH, e.g., enoxaparin.

The reference value can be a statistical function, e.g., an average, of a number of values. The reference value can be a function of another value, e.g., of the presence or distribution of a second entity present in the sample, e.g., an internal standard.

Evaluation against a reference value can be used to determine if a particular structure or chain is present in an enoxaparin sample.

Analysis of an Enoxaparin Sample Using $^1$H NMR

In some embodiments, a sample is evaluated using $^1$H NMR, e.g. a sample of a polysaccharide mixture is analyzed using $^1$H NMR. In a preferred embodiment, the sample is exchanged with $D_2O$, e.g., the sample is dissolved in $D_2O$ and lyophilized (e.g., lyophilized overnight) at least about 1, 2, 3, 4, or 5 times. The sample is then dissolved in a solvent such as $D_2O$ and placed in an NMR tube for analysis and run on a 300 MHz instrument or greater e.g., 300 MHz, 400 MHz, 500 MHz, 600 MHz, 700 MHz, 800 MHz, or 900 MHz; at 10° C. to 60° C. The recycle delay is preferably set to about 5 times the longitudinal relaxation time (T1) of the slowest relaxing proton in the mixture. In the case of an enoxaparin preparation, T1 is about 3.1 seconds at 30° C. and 600 MHz. Therefore, when analyzing an enoxaparin preparation, the recycle delay is generally set to a minimum of about 16 seconds during acquisition. Typically, from 1 to 16384 (e.g., 16 to 256) scans are collected. The peaks are then optionally integrated.

In some embodiments the anomeric region of a 1H NMR, i.e., the region from about 5 ppm to about 6 ppm, can provide useful information about the environment of H-1 protons in a polysaccharide mixture such as demonstrated in the $^1$H NMR spectrum of LOVENOX® provided in FIG. 1 (e.g., peaks 4, 5, 6, 7, and 8). The resolution of NMR spectrum in this region can provide a definitive assignment arising from a particular monosaccharide structure in the polysaccharide mixture. Additionally, other well resolved peaks from about 2 ppm to about 3.5 ppm can allow the determination of the relative percentage composition of different monosaccharides in a polysaccharide mixture such as an enoxaparin preparation (e.g., peaks 2 and 3 of FIG. 1).

The signals at approximately 5.95 ppm and 5.85 ppm in enoxaparin sodium arise from the H-4 of the non-reducing end monosaccahrides ΔU2S and ΔU. Because the cleavage chemistry used to generate enoxaparin results in the formation of these residues at the non-reducing end of chains, these signals are observed in a 1D $^1$H NMR spectrum.

Figure 2A:
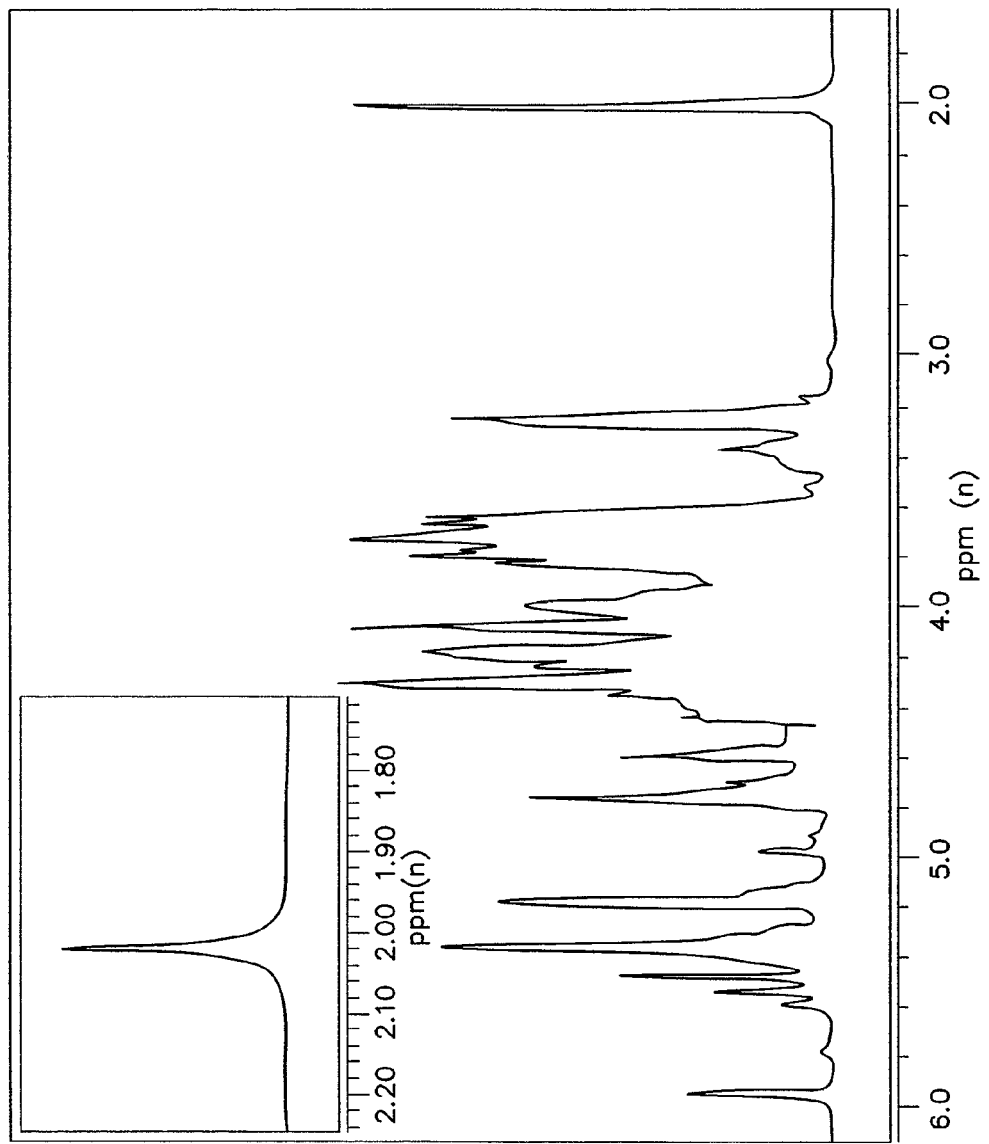
FIGS. 2a and 2b are $^1$H NMR spectra of two samples of enoxaparin preparations. (These two FIGS. 2a and 2b are inverted, needs to be corrected).
Figure 2B:
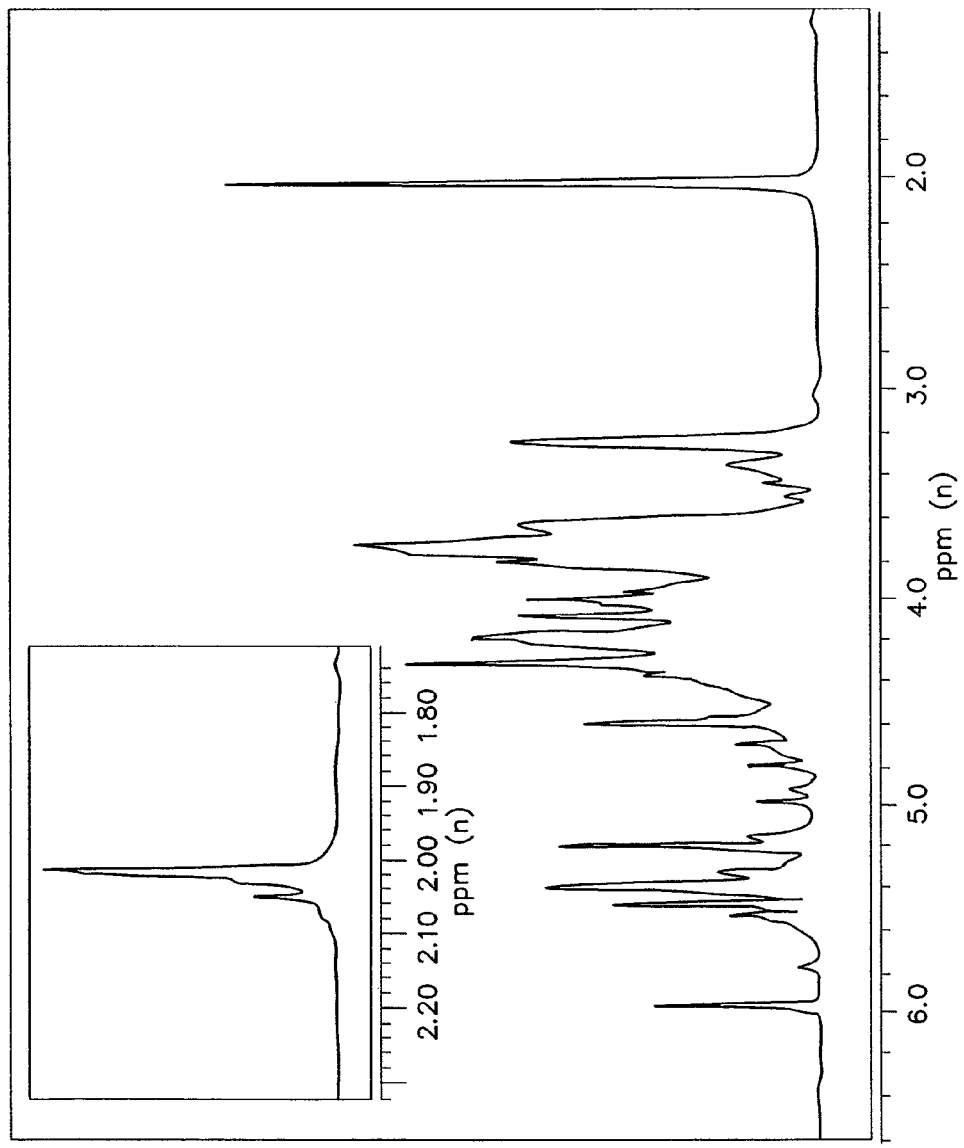

In some embodiments, a polysaccharide sample can be evaluated for the absence of one or more peaks or the lack of splitting of one or more peaks. For example, the presence of dermatan sulfate in a sample of UFH or an enoxaparin preparation can be detected using 1H NMR by observing a split in the N-acetyl peak at 2.02 ppm present in UFH or an enoxaparin preparation corresponding to N-acetylglucosamine (e.g., peak 1 of FIG. 1). In contrast to UFH and an enoxaparin preparation, dermatan sulfate contains N-acetylgalactosamine, having a proton peak from about 2.06 ppm to about 2.09 ppm. The presence of dermatan sulfate in a sample of UFH or an enoxaparin preparation would cause the N-acetylglucosamine peak at 2.02 ppm to split, due to proximity to the nearby N-acetylgalactosamine peak of the dermatan sulfate at from about 2.06 ppm to about 2.09 ppm. Referring to FIGS. 2a and 2b, an enoxaparin sample containing dermatan sulfate is can be identified by observation of a splitting of the peak from about 2.20 ppm to about 2.09 ppm as shown in FIG. 2a. An enoxaparin sample essentially free of dermatan sulfate does not demonstrate splitting of the N-acetylglucosamine peak at about 2.02 ppm as shown in FIG. 2b.

In some embodiments, an enoxaparin preparation is analyzed by $^1$H NMR to provide the total glucosamine content (TG). TG can be determined, for example, using the following mathematical relationship of the peaks identified in Table 1: TG=Total glucosamine content=P2+(P6−P8)+(P1/3).

In some embodiments, an enoxaparin preparation is analyzed by $^1$H NMR to provide the total uronic acid content (TU). TU can be determined, for example, using the following mathematical relationship of the peaks identified in Table 1: TU=Total Uronic acid content=P8+P7+P5+P4+P3−(P6−P8)

In some embodiments, an enoxaparin preparation is analyzed by $^1$H NMR to provide the relative percentage of glucosamine residues (H) or uronic acid residues in a sample (UG). For example, the following monosaccharide compositions can be analyzed, for example, to determine relative amount within an enoxaparin preparation as follows:

Glucosamine (H) residues:

| | |
|---|---|
| N-sulfated glucosamine = | (P2/TG) * 100% |
| 3-O-sulfated glucosamine = | ((P6 − P8)/TG) * 100% |
| N-acetylglucosamine = | ((P1/3)/TG) * 100% |

Uronic Acid (UG) residues

| | |
|---|---|
| Glucuronic acid = | ((P3 − (P6 − P8)/TU) * 100% |
| Ido = | (P4/TU) * 100% |
| Ido2S = | (P5/TU) * 100% |
| ΔU = | (P7/TU) * 100% |
| ΔU2S = | (P8/TU) * 100% |

In another embodiment, a method described herein can be used to detect the presence or amount of a structural moiety provided in Table 2 such as a glucosamine residue (e.g., N-sulfated, 3-O, N-Sulfated, or N-Acetyl) or a uronate residue (e.g., 2-O Sulfated, Unsulfated, or IdoA/GlcA).

For example, using the total relative amount of uronic acid residue compositions can be reported under the following three categories as provided below (See Table 2):

| | |
|---|---|
| 2) Non-sulfated uronic acid = | [Ido + Glucuronic acid + ΔU] |
| 3) Iduronic acid/Glucuronic acid ratio = | [Ido + Ido2S]/[Glucuronic acid] |

Analysis of an Enoxaparin Sample Using 2D NMR

Two dimensional nuclear magnetic resonance spectroscopy (2D NMR) can be used as a means of partially resolving and identifying signals with minimum signal overlap. Integration of the 2D NMR signals followed by simple calculations can facilitate a quantitative monosaccharide compositional analysis of a polysaccharide mixture such as analysis of a LMWH such as enoxaparin (e.g., enoxaparin sodium).

Moreover, 2D NMR can provide information on linkage environments of a disaccharide constituent, for example an H-U disaccharide, providing analysis of disaccharide linkages, including both qualitative and quantitative analysis. In some embodiments, 2D NMR analysis can provide information about the epimerization state of an H-U linkage, for example, providing information as to whether the epimerization state is an iduronic acid residue or a glucuronic acid residue (i.e., I or G).

In some embodiments, a 2D proton-carbon correlation spectroscopy (HSQC) experiment can provide quantitative compositional analysis on one or more glycosaminoglycan. For example, in some embodiments 2D NMR analysis can provide information about the nearest neighbor of a monosaccharide. This information can provide, for example, the sequence context in which a particular monosaccharide is present in a polysaccharide mixture, e.g., a LMWH such as enoxaparin.

In some embodiments, 2D NMR can be used to evaluate a polysaccharide mixture for the presence of one or more impurities such as dermatan sulfate. For example, the absence of a signal in the 30° C. HSQC within the proton range of 1.98-2.18 and the carbon range of 24.7-25.7 ppm can be used to confirm that dermatan sulfate is not present at levels greater than the level of detection of the instrument (e.g., at a level greater than about 1%).

In a preferred embodiment saccharide structure is evaluated using, 2D NMR, e.g., e.g., sample of a polysaccharide mixture exchanged with $D_2O$, lyophilized to dryness, and redissolved in $D_2O$. The sample is then placed in an NMR tube for analysis and run at 10° C. to 60° C. on a 300 MHz or greater spectrometer, e.g. 300 MHz, 400 MHz, 500 MHz, 600 MHz, 700 MHz, 800 MHz, or 900 MHz, with either a conventional or cryogenically-cooled probe. The HSQC spectrum is recorded with carbon decoupling during acquisition. In one embodiment, the HSQC spectrum is acquired with a gradient-enhanced HSQC pulse sequence. In a preferred embodiment, the HSQC spectrum is acquired with a sensitivity-enhanced gradient HSQC pulse sequence. The data is then acquired with 1 to 1024 scans for each of 16 to 1024 increments in the indirect $^{13}$C dimension. The polarization transfer delay is set to 2.3 ms to 3.9 ms. In one embodiment, the polarization transfer delay is set to 2.941 ms for an optimal transfer with $^1J_{CH}$ scalar couplings of 170 Hz. In a preferred embodiment, the polarization transfer delay is set to 3.22 ms for optimal transfer with $^1J_{CH}$ scalar couplings of 155 Hz.

Figure 3:
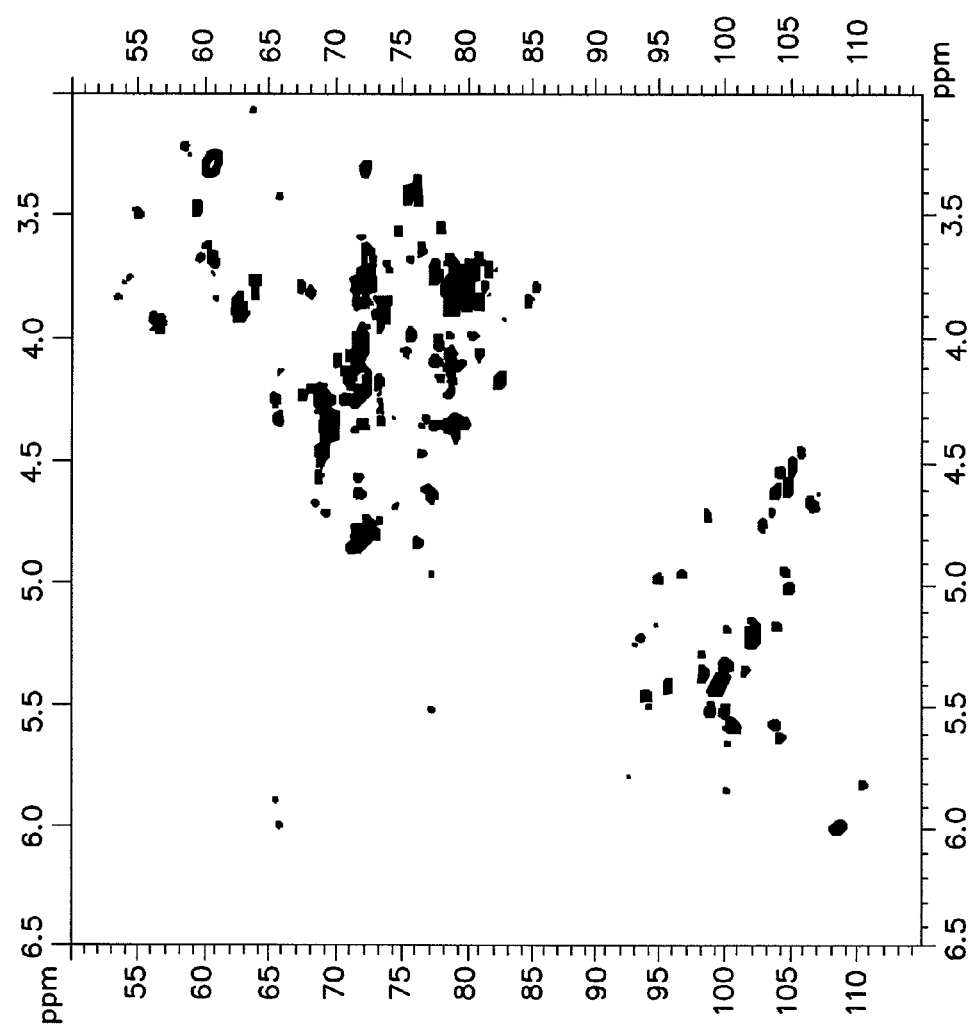
FIG. 3 is a 2D NMR spectrum of a LOVENOX® preparation.
Figure 4:
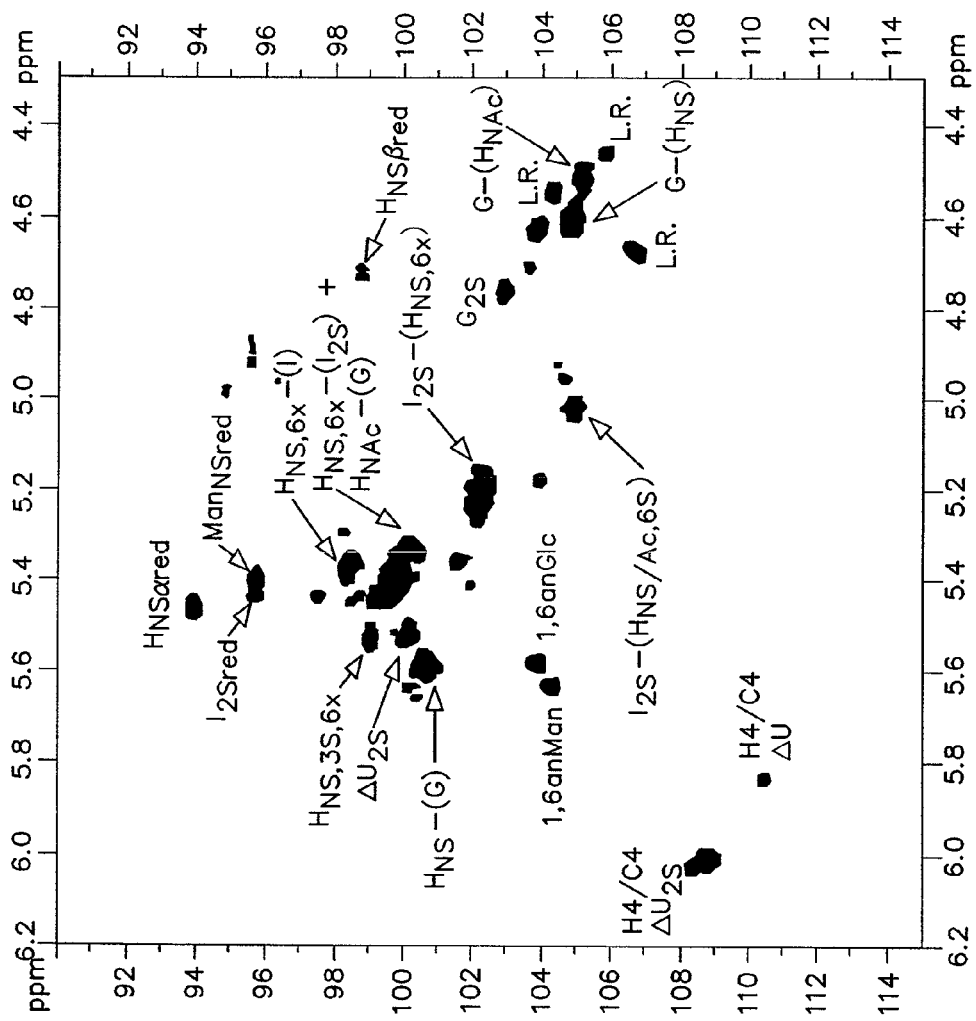
FIG. 4 is an expanded view of the 2D NMR spectrum of FIG. 3, depicting the portion of the spectrum from about 4.2 ppm to about 6.2 ppm for the proton component and from about 90 ppm to about 115 ppm for the carbon component.
Figure 5:
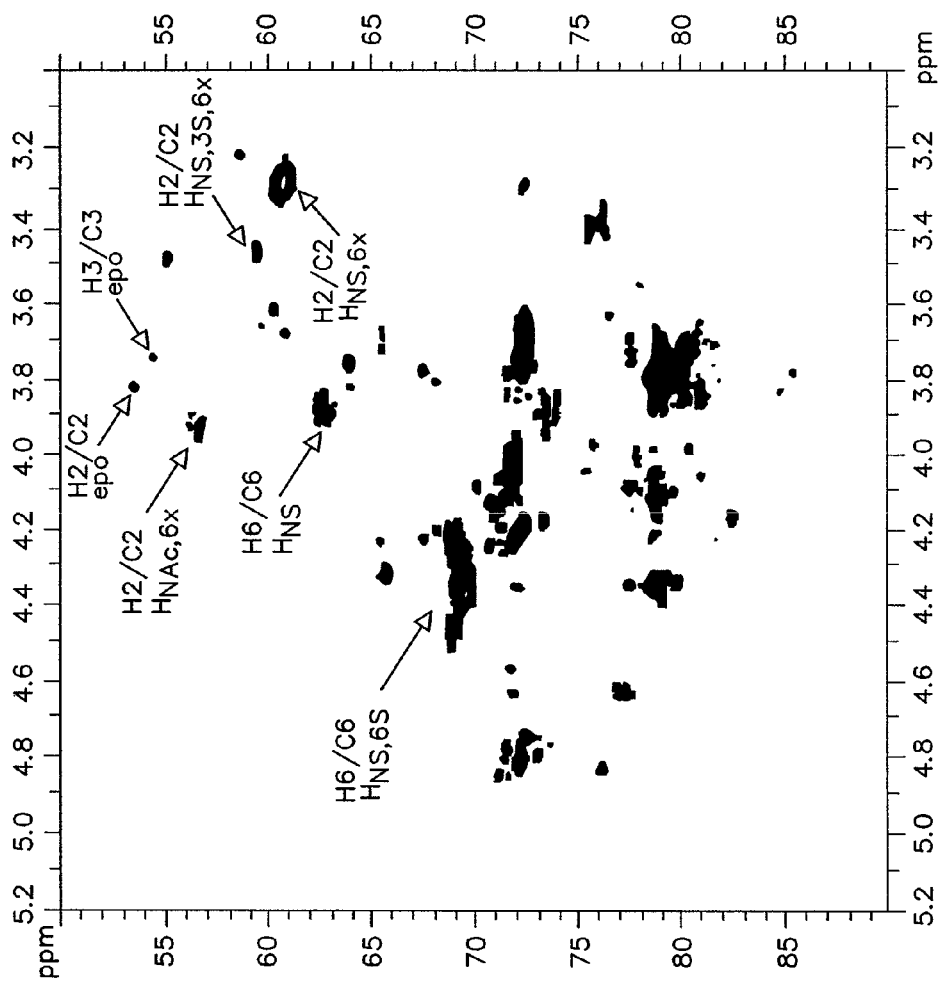
FIG. 5 is an expanded view of the 2D NMR spectrum of FIG. 3, depicting the portion of the spectrum from about 3.0 ppm to about 5.2 ppm for the proton component and from about 50 ppm to about 90 ppm for the carbon component.

The data is generally then processed and cross peaks are integrated, for example, using Bruker's XWINNMR or Topspin software. In a preferred embodiment, one or more of the following techniques is used during processing: linear prediction, zero filling, Fourier transformation, and baseline correction. In one embodiment, a non-linear transformation, e.g., Maximum Entropy Reconstuction or the Filter Diagonalization Method, is used instead of Fourier transformation. In one embodiment, a non-linear transformation is used on a sum of the experimental data and a set of synthetic signals; the synthetic signals are used to compensate for the non-linear response. Peaks are generally assigned using published chemical shifts; typical chemical shift values for various species are listed in table 4. Percent composition is calculated using the anomeric cross peak volumes, for which all uronic acid residues have similar $^1J_{CH}$ couplings as do all glucosamine residues. In some embodiments, selected H2 and H6 signals are used in the percent composition calculations along with the anomeric cross peak volumes. (See FIGS. 3, 4, and 5). The percent composition data is provided in table 3.

EXAMPLES

Example 1

Analysis of an Enoxaparin Preparation Using 1H NMR

A 12-16 mg sample of a polysaccharide mixture (e.g. a sample of enoxaparin) was exchanged three times with 0.6 ml portions of $D_2O$ (99.9% atom D; sigma), followed by lyophilization overnight, exchanging the labile protons with deuterium. The sample was dried and then dissolved again in 0.7 ml $D_2O$ (99.9% atom D; Cambridge Isotope Labs), and placed into an NMR tube (Wilmad-Labglass Inc.) for analysis. All $^1H$ NMR analysis was run on a Bruker Avance-400 MHz instrument. Spectra were acquired at 313 K to shift the water (HOD) peak upfield so that it is no longer close to the anomeric region, where the unique signals of interest are located. Since the signal for the water peak was significantly large, the water peak was presaturated during the 16 second recycle delay. Furthermore to ensure accurate integration, the recycle delay was set to about 16 s. For an improved S/N ratio 128 scans were generally collected. The peaks were then integrated.

Example 2

Analysis of an enoxaparin preparation using 2D NMR

Two-dimensional spectra were obtained at 298 K with a Bruker Advance 600 MHz spectrometer equipped with a 5-mm CPTXI cryoprobe. Samples were lyophilized from 1 mL deuterium oxide three times before being dissolved in 0.7 mL deuterium oxide (99.996 atom % D2O). Sensitivity-enhanced gradient HSQC spectra were recorded with carbon decoupling during acquisition. The data were then acquired with 16 scans for each of 128 increments in the indirect $^{13}C$ dimension. The polarization transfer delay was set to 2.941 ms for an optimal transfer with $^1J_{CH}$ scalar couplings of 170 Hz. The data was processed and cross peaks were integrated using Bruker's XWINNMR 3.5 software. Peaks were assigned using published chemical shifts. Percent composition was calculated using the anomeric cross peak volumes, for which all uronic acid residues have similar $^1J_{CH}$ couplings as do all glucosamine residues. (See FIGS. 3, 4, and 5). The percent composition data is provided in table 3.

What is claimed is:

1. A method of processing an enoxaparin preparation comprising:
    performing 2D-NMR to determine an amount of an epoxide, a reducing end 2-O sulfated uronic acid and a 1,6 anhydro mannosamine present in an enoxaparin preparation, and
    if the amount of the epoxide, the reducing end 2-O sulfated uronic acid and the 1,6 anhydro mannosamine is present in an amount within a preselected range, processing said preparation, wherein said processing includes one or more of selecting, accepting, processing into drug product, shipping, formulating, labeling, packaging or selling said preparation, and
    if the amount of the epoxide, the reducing end 2-O sulfated uronic acid or the 1,6 anhydro mannosamine is not present in an amount within the preselected range, discarding or withholding the preparation,
    wherein the preselected range of the epoxide corresponds to between 0.6 and 1.0 percent composition, wherein the preselected range of the reducing end 2-O sulfated uronic acid corresponds to between 0.8 and 1.4 percent composition, wherein the preselected range of the mannosamine corresponds to between 2.1 and 2.9 percent composition, and
    wherein the percent composition is calculated using the specific cross peak volumes for which all uronic acid residues have similar $^1J_{CH}$ couplings as do all glucosamine residues.

2. The method of claim 1, wherein the preparation has the reducing end 2-O sulfated uronic acid present in an amount that corresponds to between 0.9 and 1.3 percent composition, and the preparation is processed.

3. The method of claim 2, wherein the preparation has the reducing end 2-O sulfated uronic acid present in an amount that corresponds to between 0.9 and 1.2 percent composition, and the preparation is processed.

4. The method of claim 1, wherein the preparation has the epoxide present in an amount that corresponds to between 0.65 and 0.95 percent composition, and the preparation is processed.

5. The method of claim 4, wherein the preparation has the epoxide present in an amount that corresponds to between 0.7 and 0.9 percent composition, and the preparation is processed.

6. The method of claim 1, wherein the preparation has the 1,6 anhydro mannosamine present in an amount that corresponds to between 2.2 and 2.8 percent composition, and the preparation is processed.

7. The method of claim 6, wherein the preparation has the 1,6 anhydro mannosamine present in an amount that corresponds to between 2.3 and 2.7 percent composition, and the preparation is processed.

8. The method of claim 1, wherein the NMR-based determination further includes an amount of total 1,6 anhydrohexosamine and if the amount of the epoxide, the reducing end 2-O sulfated uronic acid, the 1,6 anhydro mannosamine, and total 1,6 anhydrohexosamine is present in an amount within the preselected range for the epoxide, the preselected range for the 2-O sulfated uronic acid, the preselected range for the 1,6 anhydro mannosamine, and a preselected range for the total 1,6 anhydrohexosamine, processing said preparation, and if the amount of the epoxide, the reducing end 2-O sulfated uronic acid, the 1,6 anhydro mannosamine, or total 1,6 anhydrohexosamine is not present in an amount within the preselected range, discarding or withholding the preparation, wherein the preselected range of the total 1,6 anhydrohexosamine corresponds to between 4.6 and 5.8 percent composition.

9. The method of claim 8, wherein the preparation has the total 1,6 anhydrohexosamine present in an amount that corresponds to between 5.0 and 5.6 percent composition, and the preparation is processed.

10. The method of claim 8, wherein the preparation has the total 1,6 anhydrohexosamine present in an amount that corresponds to between 5.2 and 5.4 percent composition, and the preparation is processed.

11. The method of claim 1, wherein the enoxaparin preparation comprises an enoxaparin drug substance.

12. The method of claim 1, wherein the processing comprises processing into a drug product.

13. The method of claim 12, wherein the enoxaparin preparation comprises an enoxaparin drug substance.

14. The method of claim 1, wherein the processing comprises formulating.

15. The method of claim 14, wherein the enoxaparin preparation comprises an enoxaparin drug substance.

16. The method of claim 1, wherein the preselected range is determined from a reference sample selected from the group consisting of a commercially available sample, a sample from a previous production, a production standard imposed by a regulatory agency, and a release standard.

17. The method of claim 16, wherein the reference sample is a commercially available sample.

18. The method of claim 16, wherein the reference sample is a sample from previous production.

19. The method of claim 16, wherein the reference sample is a production standard imposed by a regulatory agency.

20. The method of claim 16, wherein the reference sample is a release standard.

21. A method of processing an enoxaparin preparation comprising:
    performing 2D-NMR to determine a total amount of N-sulfated hexosamine ($H_{NS}$), a total amount of 1,6 anhydrohexosamine, a total amount of 2-O-sulfated uronic acid, a total amount of 3-O-sulfated glucosamine ($H_{NS,3S,6S}$), a total amount of N-acetyl glucosamine ($N_{NAc}$), a total amount of 6-O-sulfated glucosamine ($H_{6S}$), a total amount of non-sulfated uronic acid and a total amount of epoxide in an enoxaparin preparation,
    comparing the total amount of N-sulfated hexosamine ($H_{NS}$), 1,6 anhydrohexosamine, 2-O-sulfated uronic acid, 3-O-sulfated glucosamine ($H_{NS,3S,6S}$), N-acetyl glucosamine ($H_{NAc}$), 6-O-sulfated glucosamine ($H_{6S}$), non-sulfated uronic acid and epoxide to a preselected range, wherein the preselected range corresponds to a range A, range B or range C provided in Table 3,

TABLE 3

| Monosaccharide | Percentage Composition Range A* | Percentage Composition Range B | Percentage Composition Range C |
|---|---|---|---|
| Hexosamine Residues | | | |
| Total N-sulfated hesoxamine ($H_{NS}$) | 84-88 | 80-90 | 77-95 |
| $H_{NS}$-G | 10.7-11.2 | 10.5-11.5 | 9.5-12.0 |
| $H_{NS}$-I | 7.0-8.0 | 6.7-8.0 | 6.3-8.2 |
| 1,6 An Man | 2.3-2.7 | 2.2-2.8 | 2.1-2.9 |
| 1,6 An Glc | 2.7-2.8 | 2.6-3.0 | 2.5-3.1 |
| Total 1,6 anhydro | 5.2-5.4 | 5.0-5.6 | 4.6-5.8 |
| 3-O-sulfated glucosamine ($H_{NS,3S,6S}$) | 3.9-4.4 | 3.7-4.5 | 3.5-4.6 |
| N-acetyl glucosamine ($H_{NAc}$) | 9.0-10.0 | 8.9-10.2 | 8.8-10.8 |
| 6-O-sulfated glucosamine ($H_{6S}$) | 83-88 | 78-90 | 75-92 |
| Uronic acid residues | | | |
| 2-O-sulfated uronic acid | 74-76 | 71-80 | 67-83 |
| $I_{2S,red}$ | 0.9-1.2 | 0.9-1.3 | 0.8-1.4 |
| $G_{2S}$ | 2.6-3.0 | 2.5-3.1 | 2.5-3.3 |
| Non-sulfated uronic acid | 24-26 | 23-27 | 22-28 |
| 1-$H_{NS/Ac,6S}$ | 5.3-6.4 | 5.0-6.5 | 4.7-6.5 |
| I-$H_{NS,Ac}$ | 0.90-1.40 | 0.8-1.50 | 0.8-1.55 |
| G-$H_{NS}$ | 12.5-13.5 | 11.8-13.7 | 11.3-13.9 |
| G-$H_{NAc}$ | 3.10-4.40 | 3.00-4.60 | 3.00-4.85 |
| Other residues | | | |
| Epoxide | 0.7-0.9 | 0.65-0.95 | 0.6-1.0 | wherein the percent composition is calculated using the anomeric cross peak volumes for which all uronic acid residues have similar $^1J_{CH}$ couplings as do all glucosamine residues; and, if the amounts are within the preselected range, processing said preparation, wherein processing includes one or more of selecting, accepting, processing into drug product, shipping, formulating, labeling, packaging or selling said preparation, and if the amounts are not within the preselected range, discarding or withholding the preparation.

* * * * *